United States Patent
Weikel, Jr. et al.

(10) Patent No.: US 9,668,717 B2
(45) Date of Patent: *Jun. 6, 2017

(54) BIOPSY DEVICE WITH VARIABLE SIDE APERTURE

(71) Applicant: DEVICOR MEDICAL PRODUCTS, INC., Cincinnati, OH (US)

(72) Inventors: Robert F. Weikel, Jr., Hamilton, OH (US); Lee E. Reichel, Springboro, OH (US); John A. Hibner, Mason, OH (US); Michael R. Ludzack, Maineville, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 80 days.

This patent is subject to a terminal disclaimer.

(21) Appl. No.: 14/793,816

(22) Filed: Jul. 8, 2015

(65) Prior Publication Data

US 2015/0305723 A1 Oct. 29, 2015

Related U.S. Application Data

(60) Continuation of application No. 13/594,979, filed on Aug. 27, 2012, now Pat. No. 9,095,327, which is a
(Continued)

(51) Int. Cl.
*A61B 10/02* (2006.01)

(52) U.S. Cl.
CPC ...... *A61B 10/0275* (2013.01); *A61B 10/0283* (2013.01)

(58) Field of Classification Search
CPC .................. A61B 10/0275; A61B 10/0283
See application file for complete search history.

(56) References Cited

U.S. PATENT DOCUMENTS

| 2,597,258 A | 5/1952 | Papp |
| 3,537,451 A | 11/1970 | Beck et al. |

(Continued)

FOREIGN PATENT DOCUMENTS

| AU | 2006200621 A1 | 9/2006 |
| AU | 2006200950 A1 | 9/2006 |

(Continued)

OTHER PUBLICATIONS

Canadian Office Action dated Oct. 6, 2016 for Application No. 2,931,879, 4 pages.
(Continued)

*Primary Examiner* — Rene Towa
(74) *Attorney, Agent, or Firm* — Frost Brown Todd LLC

(57) ABSTRACT

A biopsy device and method are provided for obtaining a tissue sample, such as a breast tissue biopsy sample. The biopsy device may include an outer cannula having a distal piercing tip, a cutter lumen, a side tissue port communicating with the cutter lumen, and at least one fluid passageway disposed distally of the side tissue port. The inner cutter may be advanced in the cutter lumen past the side tissue port to sever a tissue sample. After the tissue sample is severed, and before the inner cutter is retracted proximally of the side tissue port, the cutter may be used to alternately cover and uncover the fluid passageway disposed distally of the side tissue.

19 Claims, 16 Drawing Sheets

Related U.S. Application Data continuation of application No. 12/713,245, filed on Feb. 26, 2010, now Pat. No. 8,287,466, which is a continuation of application No. 12/018,451, filed on Jan. 23, 2008, now Pat. No. 7,717,861, which is a division of application No. 11/072,719, filed on Mar. 4, 2005, now Pat. No. 7,517,322.

(56) References Cited

U.S. PATENT DOCUMENTS

| | | | |
|---|---|---|---|
| 4,651,752 | A | 3/1987 | Fuerst |
| 4,958,625 | A | 9/1990 | Bates et al. |
| 5,009,640 | A | 4/1991 | Pyret et al. |
| 5,106,364 | A | 4/1992 | Hayafuji et al. |
| 5,195,533 | A | 3/1993 | Chin et al. |
| 5,256,149 | A | 10/1993 | Banik et al. |
| 5,267,970 | A | 12/1993 | Chin et al. |
| 5,313,958 | A | 5/1994 | Bauer et al. |
| 5,394,887 | A | 3/1995 | Haaga |
| 5,460,185 | A | 10/1995 | Johnson et al. |
| 5,526,822 | A | 6/1996 | Burbank et al. |
| 5,649,547 | A | 7/1997 | Ritchart et al. |
| 5,733,297 | A | 3/1998 | Wang |
| 5,769,086 | A | 6/1998 | Ritchart et al. |
| 5,775,333 | A | 7/1998 | Burbank et al. |
| 5,817,033 | A | 10/1998 | DeSantis et al. |
| 5,916,175 | A | 6/1999 | Bauer et al. |
| 5,928,164 | A | 7/1999 | Burbank et al. |
| 5,944,673 | A | 8/1999 | Gregoire et al. |
| 5,964,716 | A | 10/1999 | Gregoire et al. |
| 5,980,469 | A | 11/1999 | Burbank et al. |
| 5,989,196 | A | 11/1999 | Chu et al. |
| 6,007,497 | A | 12/1999 | Huitema |
| 6,017,316 | A | 1/2000 | Ritchart et al. |
| 6,077,230 | A | 6/2000 | Gregoire et al. |
| 6,086,544 | A | 7/2000 | Hibner et al. |
| 6,120,462 | A | 9/2000 | Hibner et al. |
| 6,142,955 | A | 11/2000 | Farascioni et al. |
| 6,165,136 | A | 12/2000 | Nishtala et al. |
| 6,217,548 | B1 | 4/2001 | Tsugita et al. |
| 6,228,055 | B1 | 5/2001 | Foerster et al. |
| 6,231,522 | B1 | 5/2001 | Voegele et al. |
| 6,244,447 | B1 | 6/2001 | Frieze et al. |
| 6,273,862 | B1 | 8/2001 | Privitera et al. |
| 6,283,925 | B1 | 9/2001 | Terwilliger |
| 6,436,054 | B1* | 8/2002 | Viola ............... A61B 10/0275 600/562 |
| 6,471,700 | B1 | 10/2002 | Burbank et al. |
| 6,485,436 | B1 | 11/2002 | Truckai et al. |
| 6,695,121 | B2 | 2/2004 | Kawashima |
| 6,749,576 | B2* | 6/2004 | Bauer ............... A61B 10/0275 600/564 |
| 6,908,440 | B2 | 6/2005 | Fisher |
| 6,962,588 | B2 | 11/2005 | Sauvageau et al. |
| 7,306,591 | B2 | 12/2007 | Thomas et al. |
| 7,419,472 | B2 | 9/2008 | Hibner et al. |
| 7,481,775 | B2 | 1/2009 | Weikel, Jr. et al. |
| 7,517,321 | B2 | 4/2009 | McCullough et al. |
| 7,517,322 | B2 | 4/2009 | Weikel, Jr. et al. |
| 7,717,861 | B2 | 5/2010 | Weikel et al. |
| 7,740,597 | B2 | 6/2010 | Cicenas et al. |
| 7,766,843 | B2 | 8/2010 | Voegele |
| 7,831,290 | B2 | 11/2010 | Hughes |
| 8,282,573 | B2 | 10/2012 | Shabaz |
| 8,287,466 | B2 | 10/2012 | Weikel, Jr. et al. |
| 9,095,327 | B2* | 8/2015 | Weikel, Jr. ......... A61B 10/0275 |
| 2002/0151822 | A1* | 10/2002 | Burdorff ............ A61B 10/0275 600/568 |
| 2003/0153926 | A1 | 8/2003 | Schmieding et al. |
| 2003/0199753 | A1 | 10/2003 | Hibner et al. |
| 2006/0200041 | A1 | 9/2006 | Weikel, Jr. et al. |
| 2007/0208272 | A1 | 9/2007 | Voegele |

FOREIGN PATENT DOCUMENTS

| | | |
|---|---|---|
| CN | 1827050 A | 9/2006 |
| CN | 1830395 A | 9/2006 |
| DE | 197 03 418 A1 | 9/1997 |
| DE | 197 09 224 A1 | 9/1998 |
| DE | 202 09 530 U1 | 8/2002 |
| DE | 202 09 525 U1 | 11/2002 |
| EP | 1698282 A1 | 9/2006 |
| EP | 1698283 A1 | 9/2006 |
| EP | 1829487 A1 | 9/2007 |
| JP | 2005-103268 A | 4/2005 |
| JP | 2005-103269 A | 4/2005 |
| JP | 2005-103270 A | 4/2005 |
| JP | 4907198 B2 | 3/2012 |
| JP | 4943022 B2 | 5/2012 |
| MX | PA06002509 A | 9/2006 |
| MX | PA06002510 A | 9/2006 |
| WO | WO 96/24289 | 8/1996 |
| WO | WO 98/50083 | 5/1997 |
| WO | WO 98/52502 | 11/1998 |
| WO | WO 99/00966 | 1/1999 |
| WO | WO 2004/075719 | 9/2004 |

OTHER PUBLICATIONS

EnCor™ MRI Specifications and Breast Biopsy System, SenoRx, 2005, pp. 102.
Weisbrod et al., Preliminary Experience with a Dual Cutting Edge Needle in Thoracic Percutaneous Fine-Needle Aspiration Biopsy, Radiology (1987) 163: 75-78.
Australian Office Action dated Sep. 21, 2011 for Application No. AU 2006200950, 3 pgs.
Canadian Office Action dated Nov. 13, 2012 for Application No. CA 2,538,400, 2 pgs.
Canadian Office Action dated Dec. 4, 2013 for Application No. CA 2,528,400, 2 pgs.
Canadian Office Action dated Mar. 31, 2015 for Application No. CA 2,528,400, 4 pgs.
Canadian Office Action dated Mar. 8, 2016 for Application No. CA 2,528,400, 3 pgs.
Canadian Office Action dated Nov. 21, 2012 for Application No. CA 2,538,406, 3 pgs.
Canadian Office Action dated Mar. 31, 2015 for Application No. CA 2,538,406, 3 pgs.
Canadian Office Action dated Jun. 30, 2016 for Application No. CA 2,931,879, 4 pgs.
Chinese Office Action dated Dec. 26, 2008 for Application No. 200610058114.7, 11 pgs.
European Search Report and Written Opinion dated Aug. 8, 2006 for Application No. 06251159.7, 6 pgs.
European Exam Report dated Mar. 26, 2007 for Application No. 06251159.7, 4 pgs.
European Exam Report dated Mar. 24, 2009 for Application No. 06251159.7, 3 pgs.
European Exam Report dated May 3, 2011 for Application No. 06251159.7, 3 pgs.
European Search Report and Written Opinion dated Aug. 8, 2006 for Application No. 06251160.6, 5 pgs.
European Exam Report dated Jul. 24, 2008 for Application No. 06251160.5, 4 pgs.
European Search Report and Written Opinion dated Jul. 16, 2007 for Application No. 07250896.7, 7 pgs.
European Exam Report dated Sep. 19, 2008 for Application No. 07250896.3, 3 pgs.
European Exam Report dated Aug. 17, 2009 for Application No. 07250896.3, 2 pgs.
European Search Report and Written Opinion dated Sep. 17, 2007 for Application No. 07251393.0, 10 pgs.
Indian Office Action dated Jun. 23, 2016 for Application No. 147/KOL/2006, 6 pgs.
Japanese Office Action dated Jul. 19, 2011 for Application No. JP 2006-058398, 2 pgs.

(56) References Cited

OTHER PUBLICATIONS

Japanese Office Action dated Jul. 19, 2011 for Application No. JP 2006-058360, 4 pgs.
Mexican Office Action dated May 27, 2011 for Application No. PA/a/2006/002510, 2 pgs.
Indian Office Action dated Sep. 20, 2016 for Application No. 148/KOL/2006, 6 pgs.
Brazilian Office Action dated Oct. 17, 2016 for Application No. PI0601015-6, 9 pgs.
Brazilian Office Action dated Oct. 19, 2016 for Application No. PI0601016-4, 8 pgs.
Indian Office Action dated Jan. 5, 2017 for Application No. 309/KOL/2007, 6 pgs.

* cited by examiner

BIOPSY DEVICE WITH VARIABLE SIDE APERTURE

PRIORITY

This application is a continuation of U.S. Ser. No. 13/594,979, which is a continuation of U.S. Ser. No. 12/713,245, filed Feb. 26, 2010, issued as U.S. Pat. No. 8,287,466 on Oct. 16, 2012, which is a continuation of U.S. Ser. No. 12/018,451, filed Jan. 23, 2008, now U.S. Pat. No. 7,717,861, which is a divisional of prior application Ser. No. 11/072,719, filed Mar. 4, 2005, now U.S. Pat. No. 7,517,322, the disclosures of which are incorporated by reference herein in their entirety.

CROSS REFERENCE TO RELATED APPLICATIONS

This application cross references and incorporates by reference the following commonly assigned patent applications: U.S. patent application Ser. No. 10/676,944, "Biopsy Instrument with Internal Specimen Collection Mechanism," filed Sep. 30, 2003 in the name of Hibner et al., now U.S. Pat. No. 7,419,472; and U.S. patent application Ser. No. 10/732,843, "Biopsy Device with Sample Tube" filed Dec. 10, 2003 in the name of Cicenas et al., now U.S. Pub. No. 2004/0153003.

FIELD OF THE INVENTION

The present invention relates in general to biopsy devices, and more particularly to biopsy devices having a cutter for severing tissue.

BACKGROUND OF THE INVENTION

The diagnosis and treatment of tissue is an ongoing area of investigation. Medical devices for obtaining tissue samples for subsequent sampling and/or testing are know in the art. For instance, a biopsy instrument now marketed under the tradename MAMMOTOME is commercially available from Ethicon Endo-Surgery, Inc. for use in obtaining breast biopsy samples.

The following patent documents disclose various biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996, and US Patent Application 2003/0199753 published Oct. 23, 2003 to Hibner et al.

These generally-known vacuum assisted core biopsy devices include desirable features wherein larger samples are drawn in by vacuum assistance and severed by a cutter. These larger samples have benefits over needle biopsies in obtaining a sample more likely to include at least a portion of a suspicious lesion for diagnostic purposes. In addition, some of these known biopsy devices are capable of taking multiple samples without having to remove the probe. This shortens the duration and inconvenience of the procedure between taking samples. In addition, this facilitates taking sufficient samples to fully excise a suspicious lesion.

Long side apertures of a probe of these biopsy devices in combination with vacuum assistance, especially with a separate vacuum lumen, have many desirable features. However, there are situations in which lesions near the skin are difficult to biopsy with a core biopsy probe. This is more often a challenge with a small breast, especially when compressed in a localization fixture that limits the choice in access direction. If the side aperture of the probe is partially exposed, then vacuum assist may be ineffective as the specimen bowl in the probe is exposed to atmospheric pressure. Further, skin may prolapse into the specimen bowl before the cutter advances into the tissue, causing gouging of the skin, increasing post-procedure pain and scarring.

Consequently, a significant need exists for a core biopsy device that is capable of taking biopsies of a suspicious lesion that is proximate to the skin.

SUMMARY OF THE INVENTION

The present invention addresses these and other problems of the prior art by providing a core biopsy device having a probe assembly with a side aperture that is selectively longitudinally sized for taking samples. A proximal blocking member may be selectively positioned in the side aperture such that a proximal portion thereof is blocked when otherwise an outer layer of skin would prolapse into the side aperture when a cutter tube is retracted and then advanced to take a tissue sample. Thereby, discomfort and disfiguring scarring is avoided while still retaining the ability to take a tissue sample of a lesion near to a patient's skin.

In one aspect consistent with aspects of the invention, an apparatus for performing a core biopsy includes a curved portion sized to correspond to a portion of the probe surrounding at least the proximal portion of the side aperture which is held thereover by an engaging structure attached to the curved portion and registered to at least partially encompass and engage the probe. A gripping portion attached to the curved portion allows for a user to longitudinally position the curved portion over the proximal portion of the side aperture when desired. Thereby, an additional capability is provided for a biopsy device even when its operation requires that a cutter tube fully retract to remove a tissue sample before a subsequent translation for taking another sample.

In another aspect of the invention, a method of performing a biopsy of a lesion near to a patient's skin may be performed by translating a cutter tube distally in a cutter lumen to a distal-most position blocking a side aperture proximate to a distal end of the cutter lumen, inserting the cutter lumen through the patient's skin with the side aperture aligned with the lesion, retracting the cutter lumen to a position distal to an outer surface of the patient's skin with a proximal portion of the side aperture extending proximally thereof, prolapsing tissue into the side aperture, and translating the cutter lumen distally to cut a tissue sample. Using the cutter tube itself to block a portion of the side aperture that is exposed outside of the patient's skin avoids gouging the skin during cutting cycles.

These and other objects and advantages of the present invention shall be made apparent from the accompanying drawings and the description thereof.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

DETAILED DESCRIPTION OF THE INVENTION

Core sampling biopsy devices are given additional flexibility to remove tissue samples that reside close to an insertion point by incorporating an ability to block a proximal portion of a side aperture in a probe, corresponding to where the outer tissue layers contact the probe when the distal portion of the side aperture is placed beside a suspicious lesion. This proximal blocking feature may be provided by a separate member attachable to generally-known biopsy devices, leveraging existing capital investments in an economical way. In the first illustrative version, a biopsy device that includes a long stroke cutter that retracts fully out of a probe between samples in order to retrieve tissue samples is thus adapted when a variable sized side aperture is desired. Alternatively, in a second illustrative version, a biopsy device that has tissue sample retrieval that is independent of cutter position is adapted to employ the cutter as the proximal blocking feature to achieve a variable sized side aperture.

Long Stroke Biopsy Device.

Figure 1:
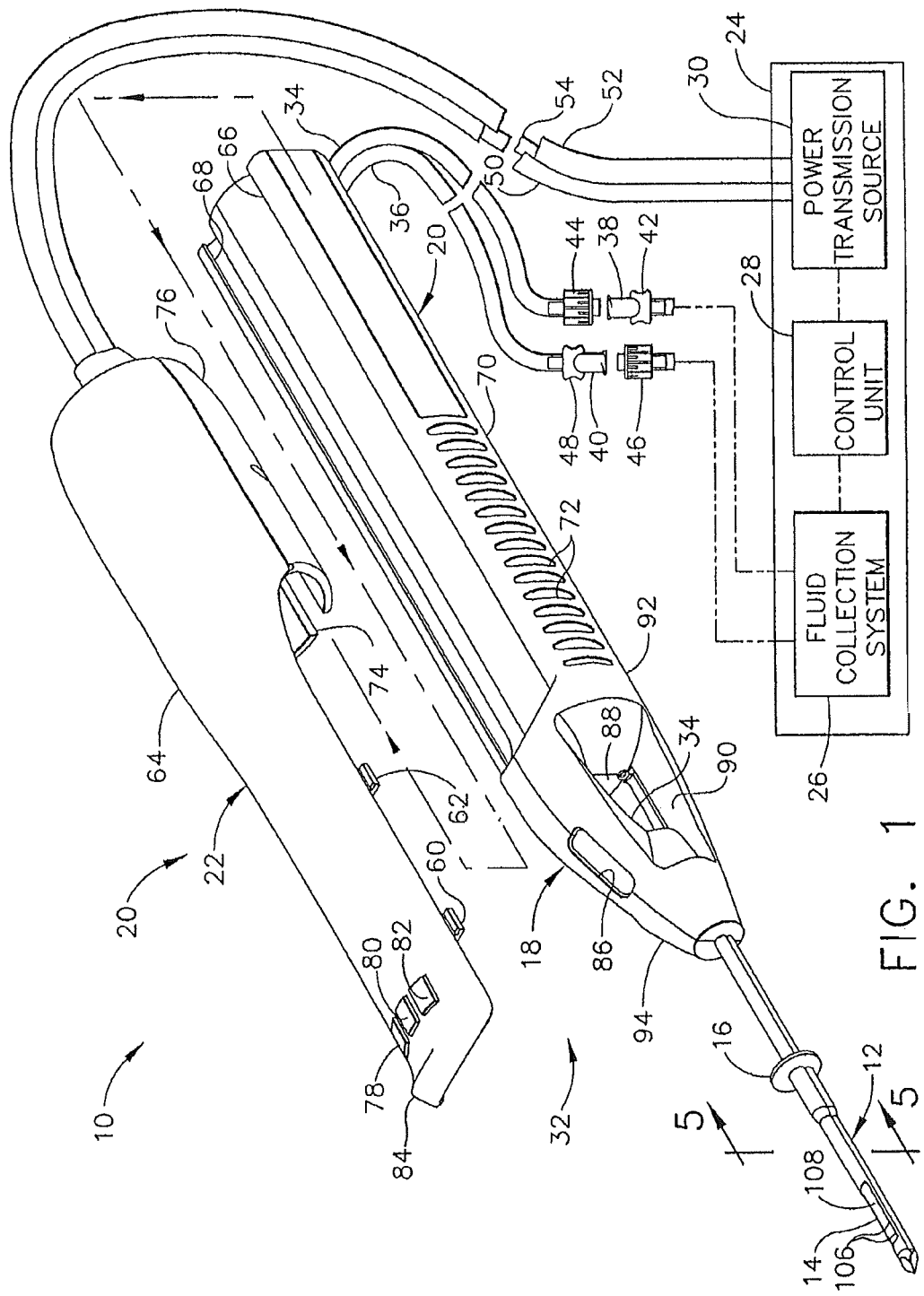
FIG. 1 is a partial isometric and partial schematic view of a core sampling biopsy system with a handpiece having a long stroke cutter for the collection of soft tissue depicted with a holster separated from a probe assembly.
Figure 2:
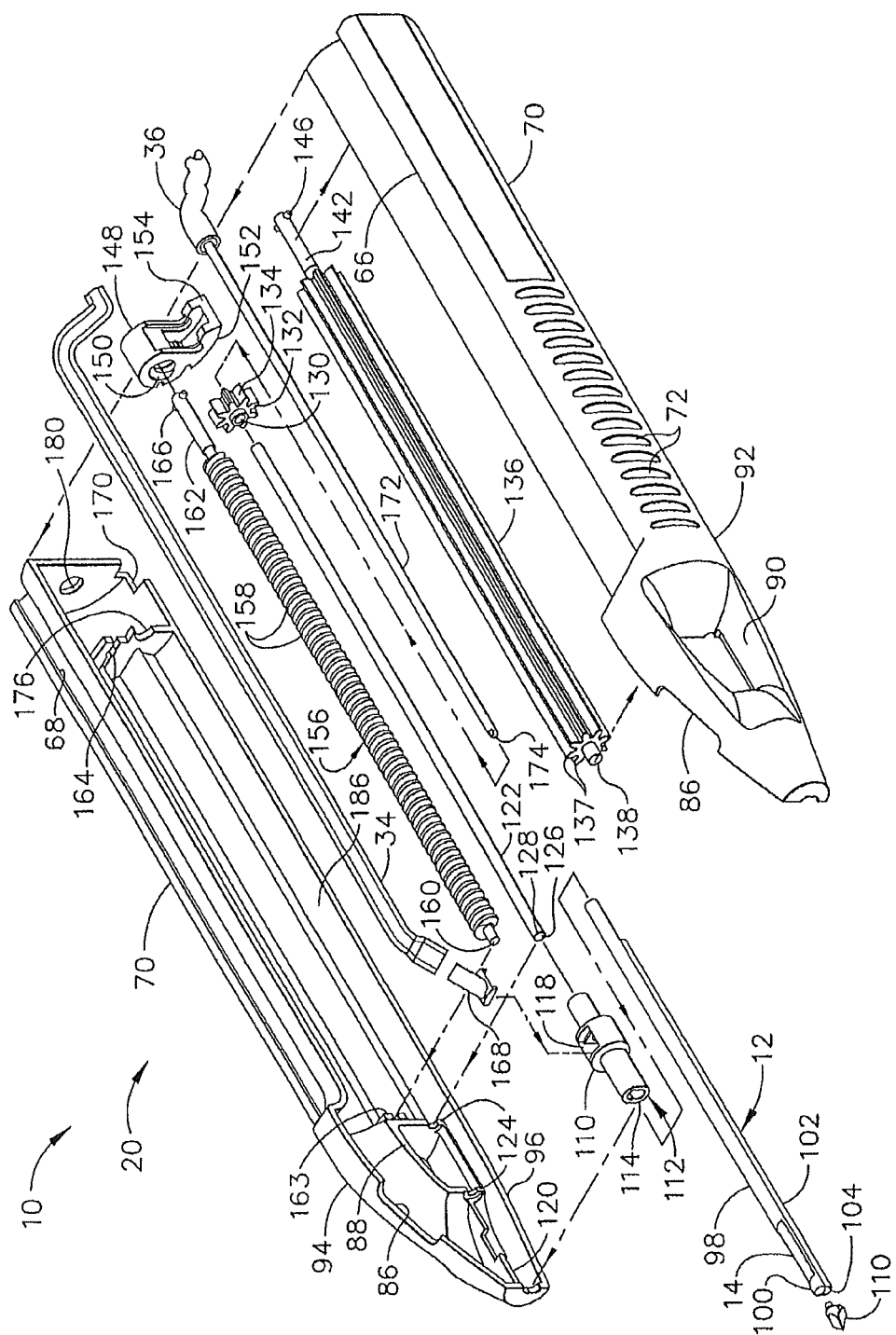
FIG. 2 is an exploded isometric view of the probe assembly of FIG. 1.
Figure 3:
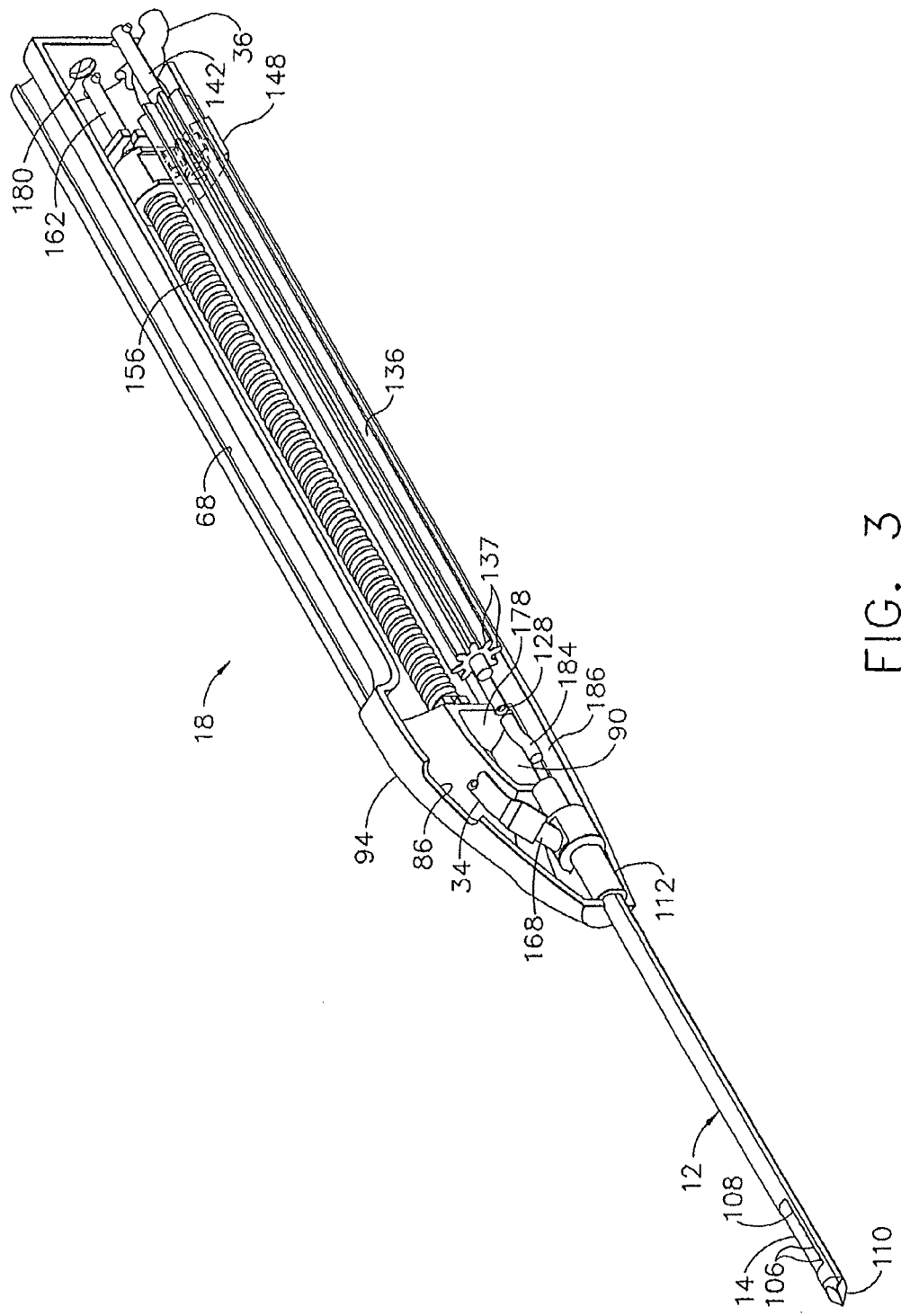
FIG. 3 is an isometric view of the probe assembly with the left handle shell removed, showing the cutter in the first, fully retracted position, and a tissue sample is shown deposited onto a tissue sampling surface of the handle after the tissue sample was removed from the distal end of the cutter.

In FIGS. 1-3, a biopsy system 10, which is described in greater detail in the previously incorporated U.S. Pat. No. 6,273,862, performs a long cutting stroke in combination with vacuum assistance to obtain a plurality of consistently sized core biopsy samples suitable for diagnostic and therapeutic treatments without the necessity of removing a probe (a.k.a. needle, piercer) 12 to retrieve each sample. While retaining a long side aperture (port) 14 in the probe 12 is useful in many instances to retrieve relatively large samples, there are instances in which a suspicious lesion has been imaged proximate to the outer skin. Positioning the probe 12 for such a biopsy would expose a proximal portion of the side aperture 14 outside of the patient's body, defeating pneumatic features of the biopsy system 10. In addition, it should be appreciated that subsequent cutting strokes may gouge away portions of the skin that may prolapse into the side aperture 14, unnecessarily increasing discomfort and scarring at the point of insertion. Advantageously, a proximal aperture blocking member, depicted in the illustrative version of FIG. 1 as a probe sleeve 16, advantageously clips onto the probe 12 and may be distally positioned to selectively cover a proximal portion of the side aperture 14 when desired.

The biopsy system 10 includes probe assembly 18 that includes a handle 20 proximally attached to the probe 12.

The biopsy system 10 further includes a detachable holster 22 that serves as a manual user interface and a mechanical and electrical connection to a control module 24 that may be remotely positioned away from diagnostic systems (e.g., magnetic resonance imaging (MRI)) (not shown). The control module 24 includes a fluid collection system 26, a control unit 28, and a power transmission source 30. The handle 20 is detachably connected to the detachable holster 22. Together they constitute a lightweight, ergonomically shaped, hand manipulatable portion referred to as a biopsy device ("handpiece") 32. The handpiece 32 is fluidly connected to the fluid collection system 26 by a first vacuum tube 34 and a second vacuum tube 36. The first and second vacuum tubes 34, 36 are detachably connected to the fluid collection system 26 by a first connector 38 and a second connector 40, respectively. The first connector 38 has a male portion 42 and a female portion 44 attached to the first vacuum tube 34. The second connector 40 has a female portion 30 and a male portion 26 attached to the second vacuum tube 36. The connector male and female portions, 42-48, are attached in this manner to prevent the accidental switching of the first and second tubes 34, 36 to the fluid collection system 26. The detachable holster 22 includes a first rotatable shaft 50, a second rotatable shaft 52, and a control cord 54. The first and second rotatable shafts 50, 52 are advantageously flexible so that the operator may easily manipulate the handpiece 32 with one hand. The control cord 54 operatively connects the handpiece 32 to the power transmission source 30 and control unit 28.

The detachable holster 22 and the handle 20 are separated in this depiction for clarity, although it would be appreciated that they would be assembled during operation. A pair of tabs 60, 62 project laterally from each side of a holster upper shell 64, and insert into left and right undercut ledges 66, 68 of a hollow handle housing 70 of the handle 20. A plurality of indentations 72 are provided on the hollow handle housing 70 to improve the operator's grip on the handpiece 32. A tube slot 74 in a lower shell 76 of the holster 22 provides clearance for first and second vacuum tubes 34, 36. A first switch 78, a second switch 80, and a third switch 82 are mounted in the distal portion of the detachable holster 22 so that the physician can operate the handpiece 32 with a single hand while having the other hand free to operate an ultrasonic imaging device or the like. The switches 78, 80, and 82 are provided to operate the power transmission source 30 and the fluid collection system 26 in conjunction with the control unit 28. A ridge 84 on the distal end of the detachable holster 22 is provided to assist the operator in grasping the handpiece 32 and in operating the switches 78, 80, and 82. The ridge 84 further provides the operator with a tactile reference as to where to properly grasp the handpiece 32.

The handle 20 includes a window 86 so that a portion of the first vacuum tube 34 may be viewed. The first and second vacuum tubes 34, 36 are made from a flexible, transparent or translucent material, such as silicone tubing. This enables visualization of the material flowing through the tubes 34, 36. By having the window 86 in the handle 20, the operator can see the flow in the first vacuum tube 34 without needing to look away from the tissue into which the probe 12 is inserted. A transverse opening 88 is provided in the distal end of the hollow handle housing 70 which allows access from either side to a tissue sampling surface 90. The tissue extracted from the surgical patient is retrieved by the operator or an assistant from the tissue sampling surface 90.

FIG. 2 is an exploded isometric view of the handle 20. The handle housing 70 is formed from a left handle shell 92 and a right handle shell 94, each injection molded from a rigid, biocompatible plastic such as polycarbonate. Upon final assembly of the handle 20, the left and right handle shells 92, 94 are joined together by ultrasonic welding along a joining edge 96, or joined by any of several other methods well known in the art.

The probe 12 includes an elongated cutter tube 98, typically metallic, defining a cutter lumen 100. On the side of the distal end of the cutter tube 98 is the side aperture 14 for receiving the tissue to be extracted from the surgical patient. Joined alongside the cutter tube 98 is an elongated, tubular, metallic vacuum chamber tube 102 defining a vacuum lumen 104. Cutter lumen 100 is in fluid communication with vacuum lumen 104 via a plurality of vacuum holes 106 located in the bottom of a "bowl" 108 defined by the side aperture 14. These holes 106 are small enough to remove the fluids but not large enough to allow excised tissue portions to be removed through the first vacuum tube 34, which is fluidly connected to the vacuum chamber tube 102. A sharpened, metallic distal end 110 is attached to the distal end of the probe 12. It is designed to penetrate soft tissue such as the breast. In this embodiment, the sharpened distal end 110 is a three-sided, pyramidal-shaped point, although the tip configuration may also have other shapes.

Still referring to FIG. 2, the proximal end of the probe 12 is attached to a union sleeve 112 having a longitudinal bore 114 through it, a widened center portion 116, and a transverse opening 118 through the widened center portion 116. The union sleeve 112 is mounted between the left and right handle shells 92, 94 on a pair of union sleeve ribs 120 projecting from each handle shell 92, 94. An elongated, metallic, tubular cutter 122 is axially aligned within the longitudinal bore 114 of the union sleeve 112 and the cutter lumen 100 of the probe 12 so that the cutter 122 may slide easily in both the distal and proximal directions. A pair of cutter guides 124 are integrally molded into each of the handle shells 92, 94 to slidably retain the cutter 122 in an coaxially aligned position with the proximal end of the cutter tube 98. Cutter 122 has a sample lumen 126 through the entire length of the cutter 122. The distal end of the cutter 122 is sharpened to form a cutter blade 128 for cutting tissue held against the cutter blade 128 as the cutter 122 is rotated. The proximal end of the cutter 122 is attached to the inside of a cutter gear bore 130 of a cutter gear 132. The cutter gear 132 may be metallic or polymeric, and has a plurality of cutter gear teeth 134, each tooth having a typical spur gear tooth configuration as is well known in the art.

Still in FIG. 2, the cutter gear 132 is driven by an elongated drive gear 136 having a plurality of drive gear teeth 106 designed to mesh with the cutter gear teeth 134. The function of the drive gear 136 is to rotate the cutter gear 132 and the cutter 122 as they translate in both longitudinal directions. The drive gear 136 may be made from a metal such as stainless steel for durability and strength or from a nonferrous material for MRI compatibility. A distal drive axle 138 projects from the distal end of the drive gear 136 and mounts into an axle support rib 140 molded on the inside of the left handle shell 92. A gear shaft 142 projects from the proximal end of the drive gear 136 and is supported by a gear shaft support rib (not shown) also molded on the inside of the left handle shell 92. A left cross pin 146 is attached to the proximal end of the gear shaft 142 as a means for rotationally engaging the drive gear 136.

Still referring to FIG. 2, a carriage 148 is provided to hold the cutter gear 132 and to carry the cutter gear 132 as it is rotated in the distal and proximal directions. In the illustrative version, the carriage 148 is molded from a rigid polymer and is cylindrically shaped with a threaded bore 150 through it and with a carriage foot 152 extending from its side. The foot 152 has a recess 154 formed into it for rotatably holding the cutter gear 132 in the proper orientation for the cutter gear teeth 134 to mesh properly with the drive gear teeth 137. The carriage 148 is attached via the threaded bore 150 to an elongated screw 156 which is parallel to the drive gear 136. The screw 156 has a plurality of conventional lead screw threads 158 and may be made from a stainless steel. The rotation of the screw 156 in one direction causes the carriage 148 to move distally, while the reverse rotation of the screw 156 causes the carriage 148 to move proximally. In turn, the cutter gear 132 moves distally and proximally according to the direction of the screw rotation, and the cutter 122 is advanced or retracted. In this version, the screw 156 is shown with a right hand thread so that clockwise rotation (looking from the proximal to distal direction) causes the carriage 148 to translate in the distal direction. It is also possible to use a left hand thread for the screw 156 as long as provisions are made to do so in the control unit 28. A distal screw axle 160 and a proximal screw shaft 162 project from the distal and proximal ends, respectively, of the screw 156. The distal screw axle 160 mounts rotatably in a distal screw support 48 of the right handle shell 94 while the proximal screw shaft 162 mounts rotatably in a proximal screw support 164, also in the right handle shell 94. A right cross pin 166 is attached to the proximal end of the screw shaft 162 as a rotational engagement means.

FIGS. 2-3 also show the first and second vacuum tubes 34, 36 referred to earlier. The distal end of the first vacuum tube 34 is attached to a polymeric vacuum fitting 168 that inserts tightly into the transverse opening 118 of the union sleeve 112. This allows the communication of fluids in the cutter lumen 100 to the fluid collection system 26. The first vacuum tube 34 is contained within the hollow handle housing 70 in an open space above the screw 156 and drive gear 136, and exits the distal end of the hollow handle housing 70 through an opening 170. The second vacuum tube 36 is fluidly attached to the proximal end of an elongated, metallic, tubular tissue remover 172. The second vacuum tube 36 exits the hollow handle housing 70 alongside the first vacuum tube 34 out the opening 170. A strainer 174 is attached to the distal end of the tissue remover 172 to prevent the passage of fragmented tissue portions through it and into the fluid collection system 26. The tissue remover 172 inserts slideably into the tubular cutter 122. During operation of the biopsy instrument, the tissue remover 172 is always stationary and is mounted between a pair of proximal supports 176 on the inside of the left and right handle shells 92, 94. When the cutter 122 is fully retracted to the first position, the distal end of the tissue remover 172 is approximately even with the distal end of the cutter 122. The distal end of the cutter 122 when at its first, fully retracted position, is slightly distal to a vertical wall 178 which is proximal and perpendicular to the tissue sampling surface 90.

In FIG. 3, a right access hole 180 is shown in the proximal end of the right handle shell 43. The right access hole 180 provides access to the proximal end of the screw 156 for operational engagement to the power transmission source 30. Similarly, a left access hole (not shown) is provided in the left handle shell 92 to provide access to the proximal end of the drive gear 136 for operational engagement with the power transmission source 30.

The tissue remover 172 has two functions. First, it helps to evacuate fluids contained in the cutter lumen 100. This is accomplished by the attachment of the second vacuum tube 36 to the proximal end of the tissue remover 172. Since the distal end of the tissue remover 172 is inserted into the cutter lumen 100, the cutter lumen 100 is fluidly connected to the fluid collection system 26. Second, the tissue remover 172 removes tissue from the cutter 122 as follows. When a tissue sample is taken, the cutter 122 advances to the fourth position just distal to the side aperture 14, and a severed tissue portion 184 is captured within the sample lumen 126 in the distal end of the cutter 122. Then the cutter 122 translates to the first position so that the cutter blade 128 is just distal of vertical wall 178. At this position of the cutter 122, the distal end of the tissue remover 172 (which is always stationary) is approximately even with the distal end of the cutter 122. Therefore, any tissue portion of significant size contained within the sample lumen 126 is pushed out of the sample lumen 126 and onto the tissue sampling surface 90. The tissue portion 184 may then be retrieved by the operator or an assistant.

With particular reference to FIG. 3, an isometric view of the handle 20 with the left handle shell 92 removed reveals the placement of the components described for FIG. 3. Part of the first vacuum tube 34 has also been removed for clarity. The carriage 148 is shown in the fully retracted position so that the cutter 122 is also at the fully retracted, or first position. The cutter blade 128 is slightly distal to the vertical wall 178 on the handle housing 70. The foot 152 of the carriage 148 is adapted to slide along a carriage guide surface 186 on the inside bottom of the hollow handle housing 70. A cutter axial transmission 188 includes the carriage 148, the screw 156, and the screw shaft 162. A cutter rotational transmission 190 includes the drive gear 136, the cutter gear 132, and the gear shaft 142.

Figure 4:
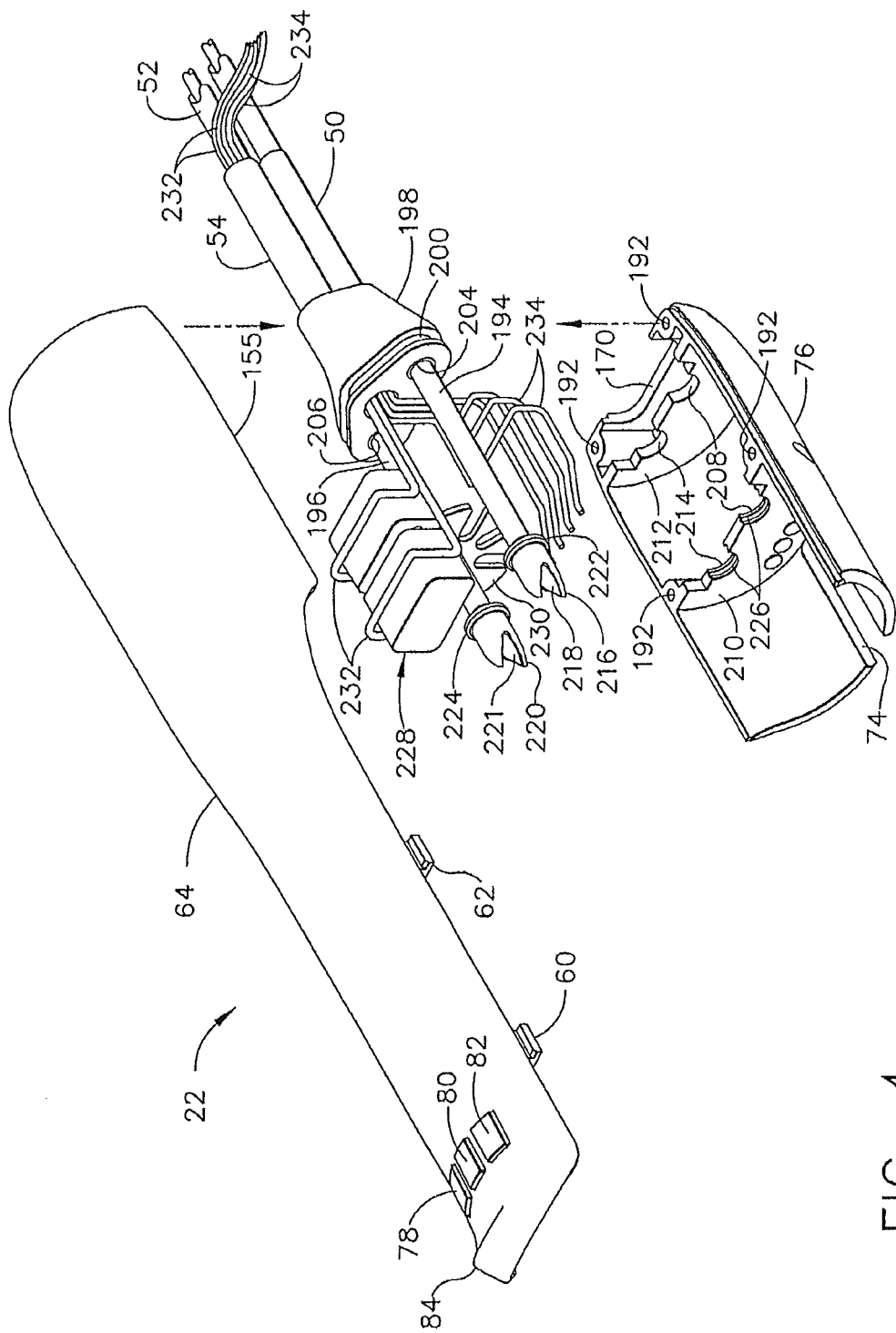
FIG. 4 is an exploded isometric view of the holster.

FIG. 4 is an exploded isometric view of the detachable holster 22. The holster upper shell 64 and a holster lower shell 76 are each injection molded from a rigid, biocompatible plastic such as polycarbonate. Upon final assembly, the shells 64, 76 are joined together by screws (not shown) or other types of fasteners well known in the art, into a plurality of alignment holes 192. A gear drive shaft 194 and a screw drive shaft 196 are contained within the proximal, enclosed portion of the detachable holster 22. These shafts extend from a grommet 198 which has a groove 200 for retainably mounting onto a shell edge 202 of both holster upper and lower shells 64, 76, respectively. The grommet 198 rotatably attaches the first rotatable shaft 50 to the gear drive shaft 194 and the second rotatable shaft 52 to the screw drive shaft 196. The first rotatable shaft 50 rotatably inserts into a left bore 204 of the grommet 198. The second rotatable shaft 52 rotatably inserts into a right bore 206. The grommet 198 also provides a strain-relieved attachment of the control cord 54 to the detachable holster 22.

Still referring to FIG. 4, the gear drive shaft 194 is supported rotatably upon a pair of gear drive mounts 208 formed into a first wall 210 and a second wall 212 of the inside of the upper and lower holster shells 64, 76. The screw drive shaft 196 is likewise supported rotatably on screw drive mounts 214. A left coupler 216 is attached to the distal end of the drive gear shaft 194 and has a left coupler mouth 218 for rotational engagement with the left cross pin 146 attached to the gear shaft 142. When the handle 20 shown in FIG. 2 is attached to the detachable holster 22, the gear shaft 142 becomes rotatably engaged to the gear drive shaft 194. Similarly, the screw drive shaft 196 has a right coupler 220 with a right coupler mouth 221 which rotatably engages with the cross pin 166 of the screw shaft 162. Each of the left and right couplers 216, 220 have a coupler flange 222, 224 that rotatably insert into thrust slots 226 formed into the corresponding portions of the drive mounts 158, 160. These coupler flanges 222, 224 bear the axial loading of the drive shafts 180, 182.

Figure 4A:
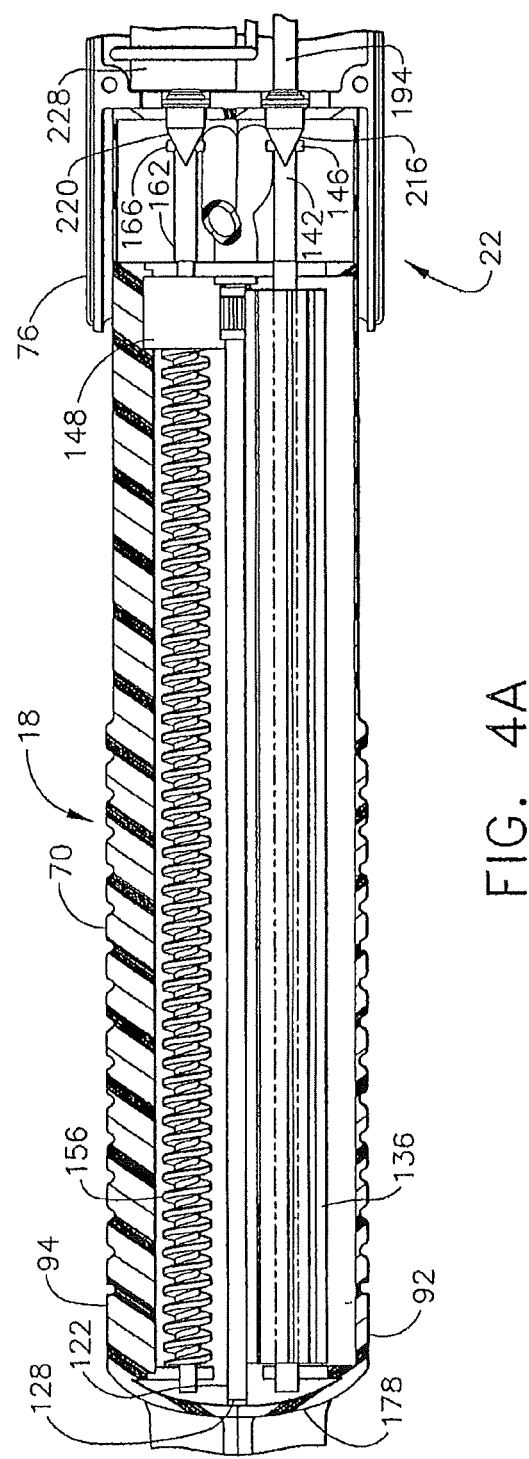
FIG. 4A is a top view in section of the probe assembly and a distal portion of the holster, revealing a cutter in a first, fully retracted position.

With reference to FIGS. 4-4A, the detachable holster 22 further includes a screw rotation sensor 228, available from Hewlett-Packard as part number HEDR-81002P, for providing an electronic signal to the control unit 28 to be described in more detail later. The rotation sensor 228 is mounted within the inside of the holster upper shell 64 and in a position directly above the screw drive shaft 196. A fluted wheel 230 is attached to the screw drive shaft 196 and extends in front of a light emitting diode (not shown) contained within the rotation sensor 228. As the fluted wheel 230 rotates, the interrupted light beams are electronically detected and transmitted back to the control unit 28 to provide information about the rotational speed of the screw drive shaft (cutter tube axial advancement or retraction speed), and the number of screw rotations from the beginning of operation (instantaneous axial position of the cutter 122). Rotation sensor leads 232 pass through the grommet 198 and are part of the bundle of conductors within the control cord 54.

The detachable holster 22 has the switches 78, 80, 82 mounted on the inside of the holster upper shell 64. The switches 78, 80, 82 are electronically connected to a plurality of conductors 234 contained in the control cord 54. The third switch 82 operates the fluid communication between the handpiece 32 and the fluid collection system 26 and also sets the control unit 28 to respond to various commands; the second switch 80 operates the movement of the cutter 122 in the proximal direction and sets the control unit 28 to respond to various commands; and the first switch 78 operates the movement of the cutter 122 in the distal direction and sets the control unit 28 to respond to various commands. The functions of the switches 78, 80, 82 are not restricted to what has been described for the first embodiment. Also, the physical locations of the switches 78, 80, 82 on the handpiece 32 are not restricted to the locations depicted in FIG. 4.

Use of Sleeve to Adjust Side Aperture of Long Stroke Biopsy Device.

Figure 5:
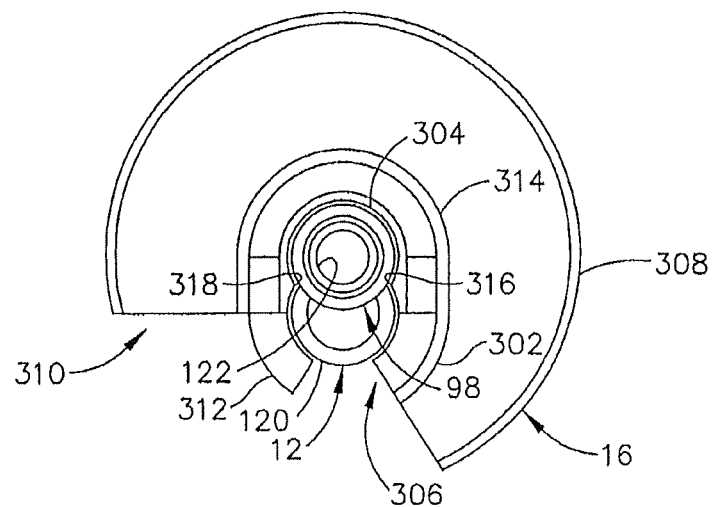
FIG. 5 is a front view in elevation of the probe and probe sleeve taken in cross section along lines 5-5 of FIG. 1.
Figure 6:
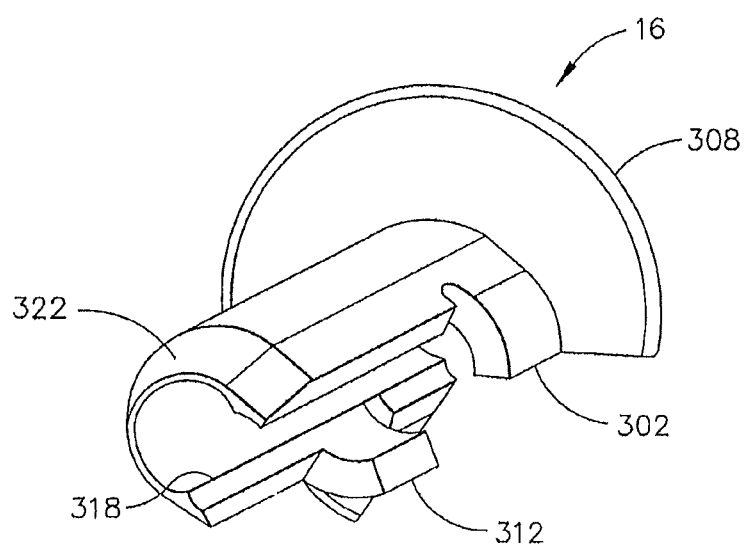
FIG. 6 is an isometric view of the probe sleeve of FIG. 1.
Figure 7A:
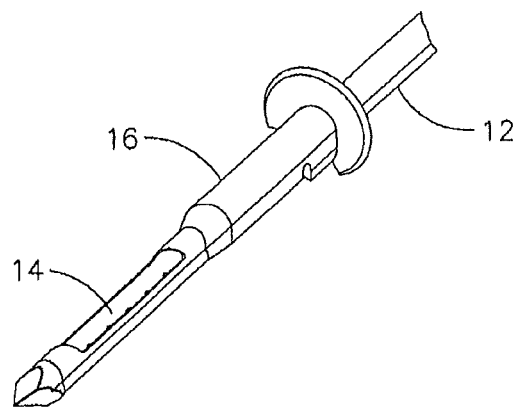
FIG. 7A is an isometric view of the probe of the biopsy system of FIG. 1 with the probe sleeve at a proximal position exposing a side aperture.
Figure 7B:
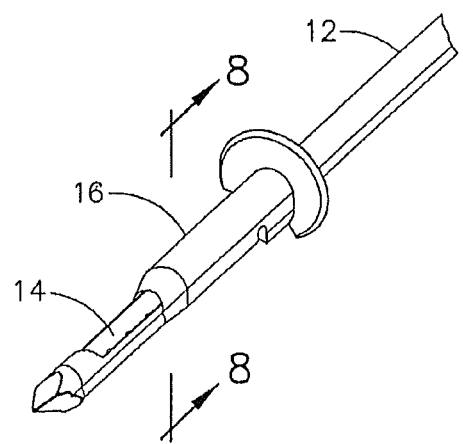
FIG. 7B is an isometric view of the probe of the biopsy system of FIG. 1 with the probe sleeve at a more distal position partially blocking the side aperture.
Figure 7C:
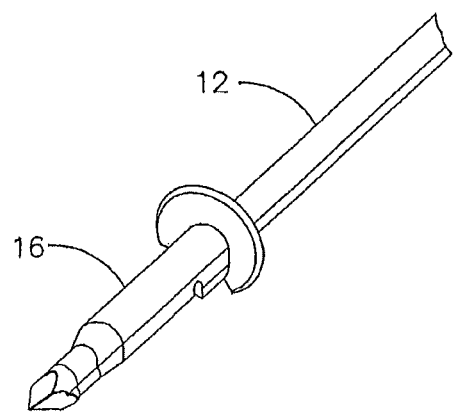
FIG. 7C is an isometric view of the probe of the biopsy system of FIG. 1 with the probe sleeve at a most distal position completely blocking the side aperture.

In FIGS. 5-6, the probe sleeve 16 is shown detached from the biopsy system 10 and advantageously is open along a lower longitudinal portion to allow for snapping onto the probe 14. In particular, a proximal collar 302 has an interrupted figure-eight inner contour 304 (FIG. 5) corresponding to a lateral cross section of the probe 12. A lower opening 306 in the proximal collar 302 flares outwardly into a flange 308 that has a wider arcing opening 310 so that a right lower portion of the proximal collar 302 extends unsupported as a flexible locking lip 312. A distally projecting half tube 314 is attached to the proximal collar 302 and overarches a top portion of the probe 12 with inwardly directed left and right ridges 316, 318 running along each lateral lower edge of the half tube 314 to longitudinally slidingly engage a pinched lateral waist 320 of the probe 12. The half tube 314 distally terminates in a beveled edge 322 (FIG. 6) to provide for smoother insertion at the insertion point into tissue, as illustrated in FIGS. 7A-7C wherein the probe sleeve 16 is first proximal to the side aperture 14 (FIG. 7A), then slid over a proximal portion of the side aperture 14 to advantageously enable a biopsy procedure to be performed very close to the surface, (FIG. 7B) and then slid further forward to completely block the side aperture 14 (FIG. 7C).

Figure 8A:
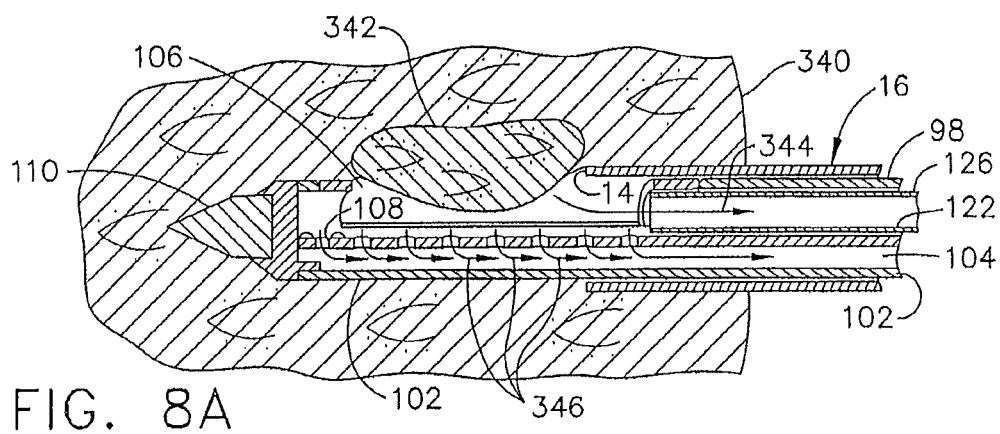
FIG. 8A is a left side view in elevation of the probe and probe sleeve of FIG. 7B taken along a longitudinal centerline of lines 8-8 with vacuum assistance being employed to prolapse tissue into a bowl of the probe.
Figure 8B:
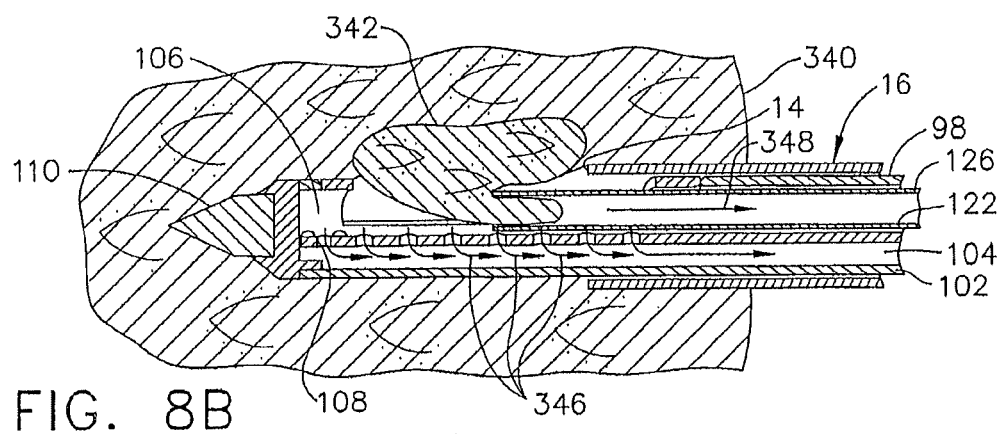
FIG. 8B is a left side view in elevation of the probe and probe sleeve of FIG. 7B taken along a longitudinal centerline of lines 8-8 with vacuum assistance being employed to prolapse tissue into a bowl and to draw severed tissue into a sample lumen as a cutter tube is rotated and translated in a cutter lumen of the probe.
Figure 8C:
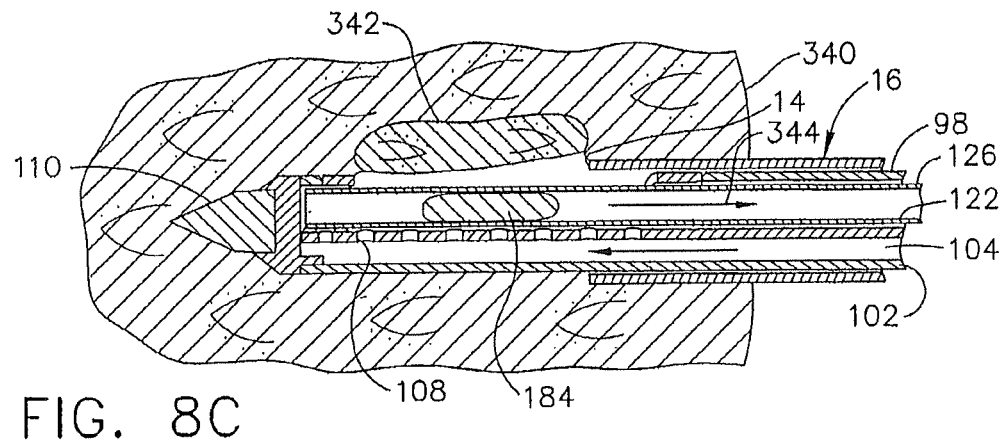
FIG. 8C is a left side view in elevation of the probe and probe sleeve of FIG. 7B taken along a longitudinal centerline of lines 8-8 with a completely severed tissue sample captured in the sample lumen.

In use, in FIG. 8A, the probe 12 has been inserted through skin 340 until the side aperture 14 has been placed adjacent to a suspicious lesion 342. Vacuum pressure as indicated by arrows 344 flows proximally through sample lumen 126, through the cutter tube 122 and, as indicated by arrows 346, through vacuum holes 108 in the bowl 106 into the vacuum lumen 104. The vacuum assistance causes a portion of the suspicious lesion 342 to prolapse into the bowl 106 of the probe 12. In FIG. 8B, the cutter tube 122 is being simultaneously rotated and distally translated to cut a biopsy sample. Vacuum continues to be drawn proximally through sample lumen 126 to assist in drawing in the severed tissue, as depicted by arrows 348, with vacuum also continuing to be drawn from the vacuum holes 108 in the bowl 106 through the vacuum lumen 104 to maintain the prolapsed tissue in the bowl 106 for cutting. In FIG. 8C, the cutter tube 122 has reached its most distal position. The tissue sample 184 is in the process of being transported out of the tissue by retracting the cutter tube 122 proximally just distal of vertical wall 178 as shown in FIG. 3 until the tissue sample 184 is ejected onto sampling surface 90 via strainer 174 as shown in FIG. 2.

Short Stroke Biopsy Device with Variable Aperture Implementation.

Figure 9:
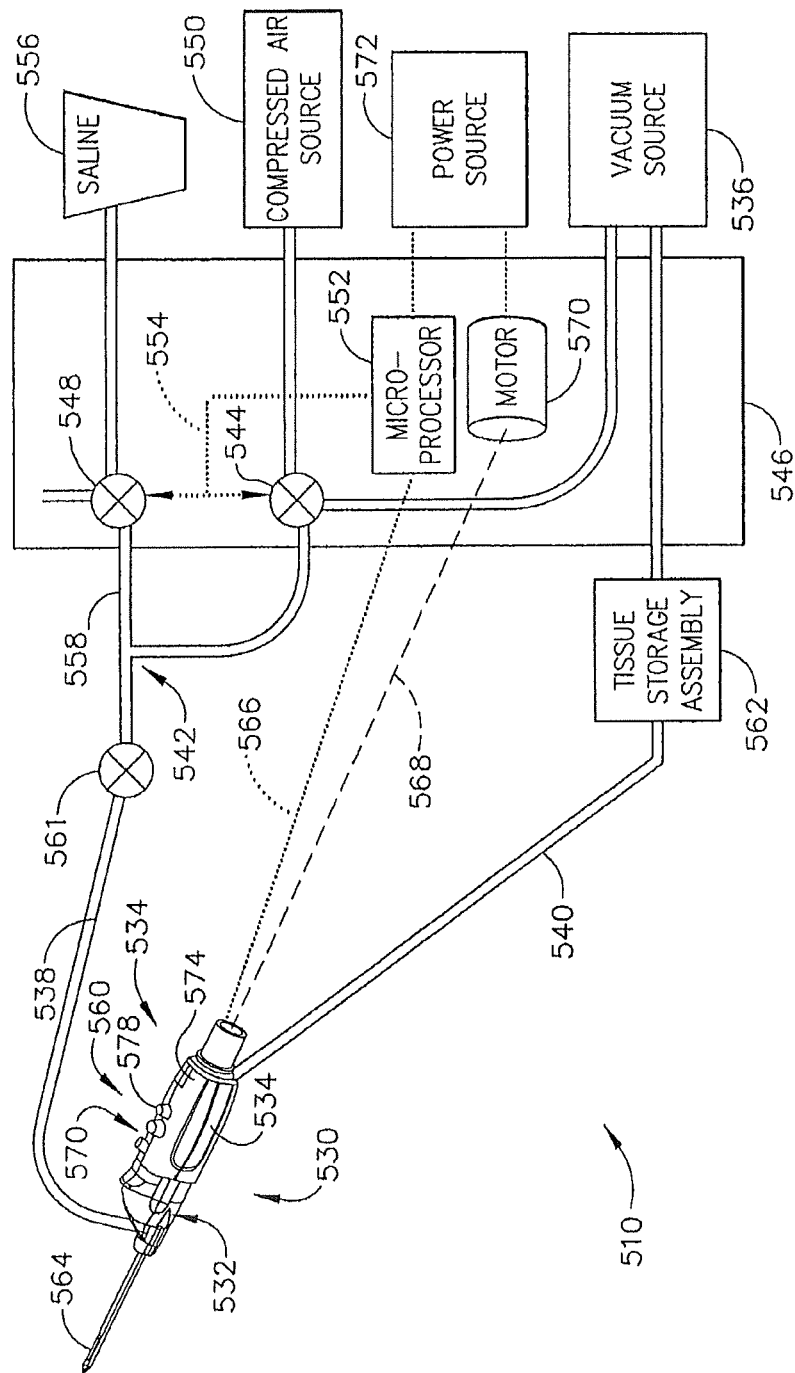
FIG. 9 is a partial isometric and partial schematic view of an alternative biopsy system that includes a handpiece with a short stroke cutter that is advantageously configured to perform a cutting stroke that blocks a proximal portion of a side aperture of a probe for taking biopsy samples near an external surface.

In the second illustrative version depicted in FIG. 9, a short stroke core sampling biopsy system 510 includes a handpiece 530 that may be held comfortably in a single hand, and may be manipulated with a single hand. Handpiece 530 may include a probe assembly 532 and a detachably connected holster 534. Probe assembly 532 may be operatively connected to a vacuum source 536, such as by a first, lateral tube 538 and a second, axial tube 540. First and second tubes 538, 540 may be made from a flexible, transparent or translucent material, such as silicon tubing, PVC tubing or polyethylene tubing. Using a transparent material enables visualization of the matter flowing through tubes 538, 540.

Figure 12:
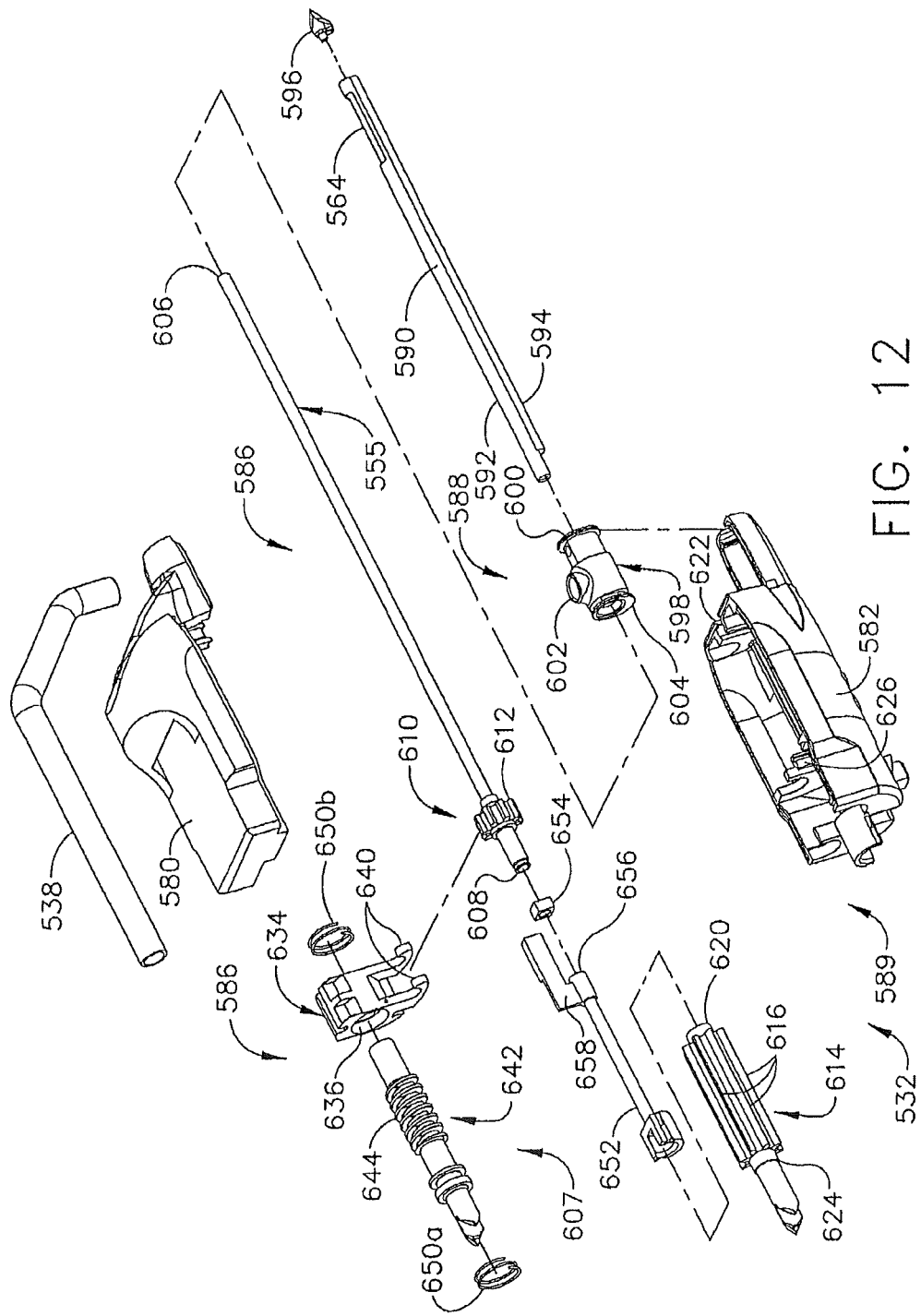
FIG. 12 is an exploded isometric view of the probe assembly of FIG. 10.

First tube 538 may includes a Y connector 542 for connecting to multiple fluid sources. A first proximal end of Y connector 542 may extend to a first solenoid controlled rotary valve 544 in a control module 546, while the second proximal end of the Y connector 542 may extend to a second solenoid controlled rotary valve 548 in control module 546. The first solenoid controlled rotary valve 544 in control module 546 may be operable to connect either the vacuum source 536 or a compressed air source 550 to lateral tube 538. It is understood within this specification that compressed air means air pressure at or above atmospheric pressure. In one configuration, when valve 544 is activated, vacuum is supplied to tube 538 from vacuum source 536, and when valve 544 is not activated, pressurized air from compressed air source 550 is supplied through tube 538. The solenoid associated with valve 544 may be controlled by a microprocessor 552 in control module 546, as indicated by dashed line 554. The microprocessor 552 may be employed to adjust the position of valve 544 automatically based upon the position of a cutter 555 (as shown in FIG. 12) movably supported within probe assembly 532. The second solenoid controlled rotary valve 548 in control module 546 may be employed to either connect a saline supply 556 (such as a saline supply bag, or alternatively, a pressurized reservoir of saline) to a tube 558 or to seal off the proximal end of tube 558. For instance, rotary valve 548 may be activated by microprocessor 552 to supply saline when one of switches 560 on handpiece 530 is actuated. When rotary valve 548 is activated, first rotary valve 544 may be automatically deactivated (such as by microprocessor 552) to prevent the interaction of vacuum and saline within lateral tube 538. A stopcock 561 may be included in lateral vacuum tube 538 to allow for a syringe injection of saline directly into the tube 538, if desired. For instance, a syringe injection may be employed to increase the saline pressure in the tube to dislodge any clogs that may occur, such as tissue clogging fluid passageways.

In one version, axial vacuum tube 540 may be employed to communicate vacuum from source 536 to probe assembly 532 through a tissue storage assembly 562. Axial tube 540 may provide vacuum through the cutter 555 within probe assembly 532 to assist in prolapsing tissue into a side aperture 564 prior to cutting. After cutting occurs, the vacuum in axial tube 540 may be employed to help draw a severed tissue sample from probe assembly 532 and into tissue storage assembly 562, as will be described in further detail below.

Holster 534 may include a control cord 566 for operationally connecting handpiece 530 to control module 546, and a flexible rotatable shaft 568 connecting the holster 534 to a drive motor 570. A power source 572 may be employed to provide energy to control module 546 for powering holster 534 via control cord 566. Switches 560 are mounted on holster upper shell 574 to enable an operator to use handpiece 530 with a single hand. One-handed operation allows the operator's other hand to be free, for example, to hold an ultrasonic imaging device. Switches 560 may include a two-position rocker switch 576 for manually actuating the motion of the cutter 555 (e.g. forward movement of the rocker switch moves the cutter 555 in the forward (distal) direction for tissue sampling and rearward movement of the rocker switch 576 actuates the cutter 555 in the reverse (proximal) direction. Alternatively, the cutter 555 could be automatically actuated by control module 546. An additional switch 578 may be provided on holster 534 for permitting the operator to activate saline flow on demand into lateral tube 538 (for instance, switch 578 may be configured to operate valve 548 for providing saline flow to tube 538 when switch 578 is depressed by the user).

Figure 10:
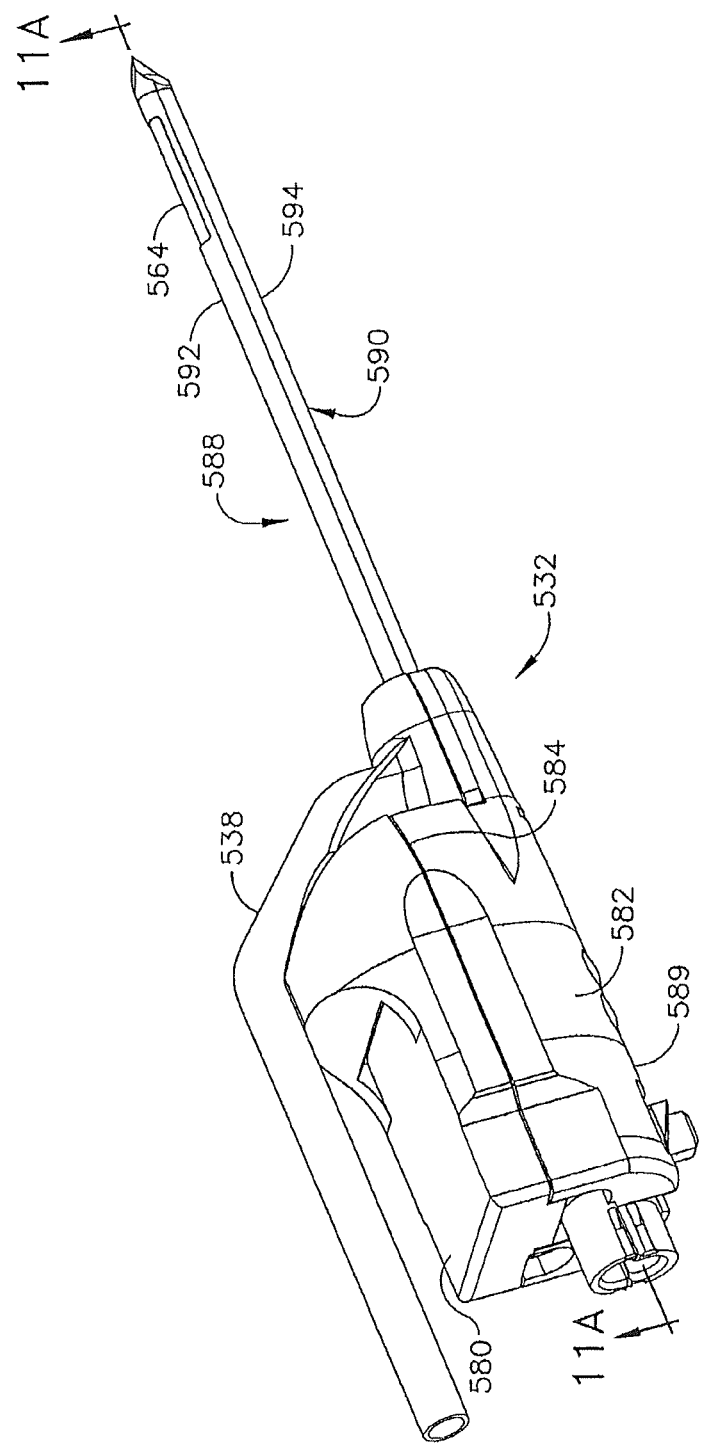
FIG. 10 is an isometric view of a probe assembly of the handpiece of FIG. 9 with a holster removed.

FIG. 10 shows probe assembly 532 disconnected from holster 534. Probe assembly 532 includes an upper shell 580 and a lower shell 582, each of which may be injection molded from a rigid, biocompatible plastic, such as a polycarbonate. Upon final assembly of probe assembly 532, upper and lower shells 580, 582 may be joined together along a joining edge 584 by any of a number of methods well-known for joining plastic parts, including, without limitation, ultrasonic welding, snap fasteners, interference fit, and adhesive joining.

Figure 11A:
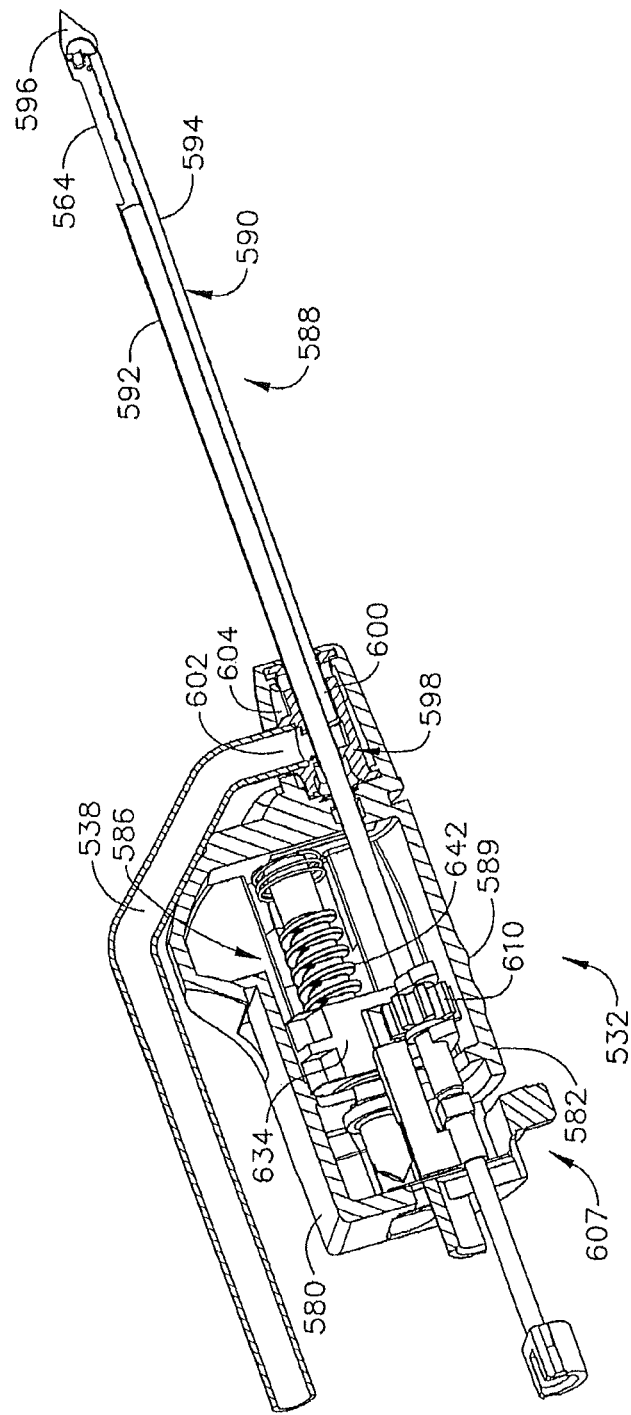
FIG. 11A is a cross-sectional isometric view of the probe assembly of FIG. 10 taken along line 11-11 with a cutter and carriage assembly positioned at a proximal position.
Figure 11B:
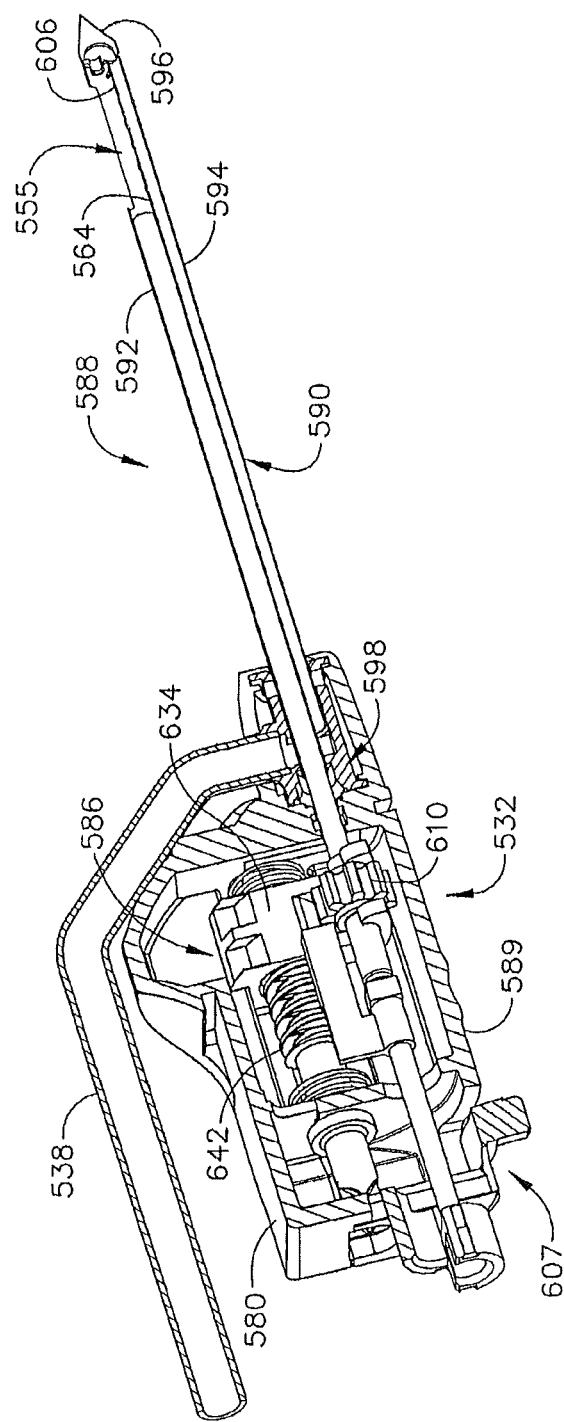
FIG. 11B is a cross-sectional isometric view of the probe assembly of FIG. 10 taken along line 11-11 with the cutter and carriage assembly positioned between proximal and distal end positions.
Figure 11C:
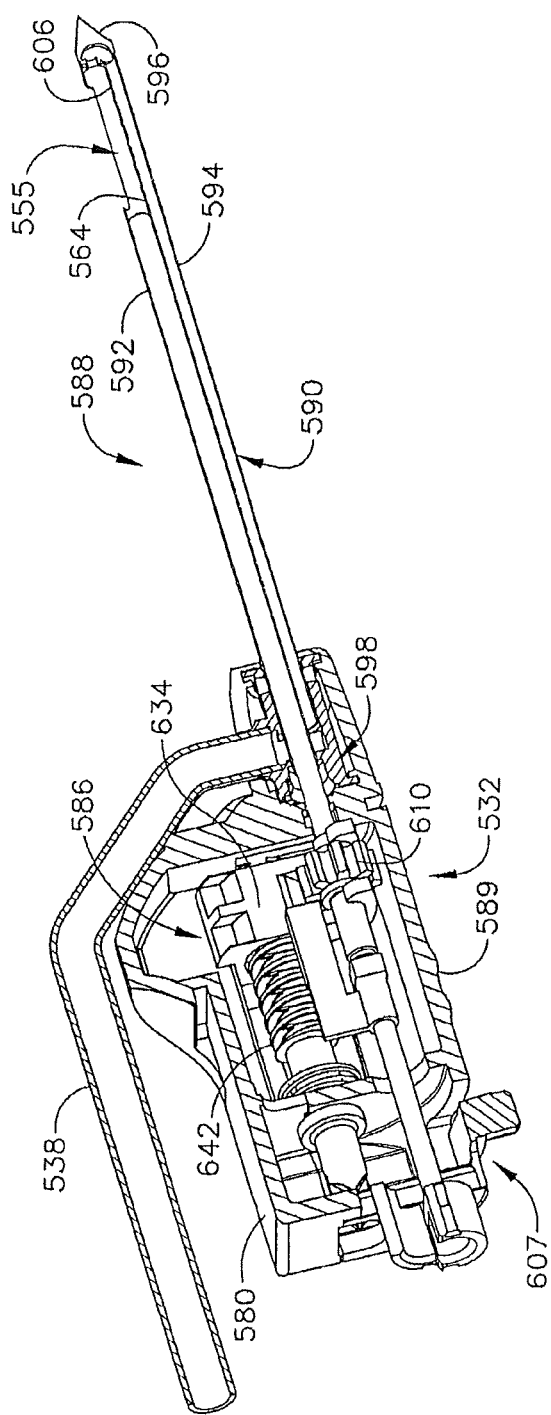
FIG. 11C is a cross-sectional isometric view of the probe assembly of FIG. 10 taken along line 11-11 with the cutter and carriage assembly positioned at the distal end position.

FIGS. 11A, 11B, 11C, and 12 illustrate probe assembly 532 in greater detail. FIG. 11A depicts a cutter assembly and carriage 586 retracted proximally. FIG. 11B depicts the cutter assembly and carriage 586 partially advanced. FIG. 11C depicts the cutter assembly and carriage 586 advanced distally. With particular reference to FIG. 12, the probe assembly 532 may include a biopsy needle (probe) 588 located at a distal end of a handle 589 of the probe assembly 532 for insertion into a patient's skin to obtain a tissue sample. Needle 588 comprises an elongated, metallic cannula 590, which may include an upper cutter lumen 592 for receiving the cutter 555 and a lower vacuum lumen 594 for providing a fluid and pneumatic passageway. Cutter 555 may be disposed within cannula 590, and may be coaxially disposed within cutter lumen 592.

Cannula 590 may have any suitable cross-sectional shape, including a circular or oval shaped cross-section. Adjacent and proximal of the distal end of cannula 590 is the side aperture 564 for receiving the tissue to be severed from the patient. The sharpened tip of needle 588 may be formed by a separate endpiece 596 attached to the distal end of cannula 590. The sharpened tip of endpiece 596 may be used to pierce the patient's skin so that the side tissue receiving port may be positioned in the tissue mass to be sampled. Endpiece 596 may have a two-sided, flat-shaped point as shown, or any number of other shapes suitable for penetrating the soft tissue of the patient.

The proximal end of needle 588 may be attached to a union sleeve 598 having a longitudinal bore 600 therethrough, and a transverse opening 602 into a widened center portion of the bore 600. The distal end of lateral tube 538 may be inserted to fit tightly into transverse opening 602 of union sleeve 598. This attachment allows the communication of fluids (gas or liquid) between the lower vacuum lumen 594 and the lateral tube 538.

The cutter 555, which may be an elongated, tubular cutter, may be disposed at least partially within upper cutter lumen 592, and may be supported for translation and rotation within cutter lumen 592. Cutter 555 may be supported within vacuum lumen 594 so as to be translatable in both the distal and proximal directions. Cutter 555 may have a sharpened distal end 606 for cutting tissue received in upper cutter lumen 592 through side aperture 564. The cutter 555 may be formed of any suitable material, including without limitation a metal, a polymer, a ceramic, or a combination of materials. Cutter 555 may be translated within cutter lumen 592 by a suitable cutter drive assembly 607 such that distal end 606 travels from a position proximal of the side aperture 564 (illustrated in FIG. 11A) to a position distal of side aperture 564 (illustrated in FIG. 11C), in order to cut tissue received in cutter lumen 592 through the side aperture 564. In an alternative embodiment, an exterior cutter (not shown) may be employed, with the exterior cutter sliding coaxially with an inner cannular needle, and the inner needle may include a side tissue receiving port.

Union sleeve 598 is supported between probe upper and lower shells 580, 582 to ensure proper alignment between cutter 555 and the union sleeve 598. The cutter 555 may be a hollow tube, with a sample lumen 608 extending axially through the length of cutter 555. The proximal end of cutter 555 may extend through an axial bore of a cutter gear 610. Cutter gear 610 may be metallic or polymeric, and includes a plurality of cutter gear teeth 612. Cutter gear 610 may be driven by a rotary drive shaft 614 having a plurality of drive gear teeth 616 designed to mesh with cutter gear teeth 612. Drive gear teeth 616 may extend along the length of drive shaft 614 so as to engage cutter gear teeth 612 as the cutter 555 translates from a proximal most position to a distal most position, as illustrated in FIGS. 11A-11C. Drive gear teeth 616 may be in continual engagement with cutter gear teeth 612 to rotate cutter 555 whenever drive shaft 614 is rotatably driven. Drive shaft 614 rotates cutter 555 as the cutter advances distally through side aperture 564 for the cutting of tissue. Drive shaft 614 may be injection molded from a rigid engineered plastic such as liquid crystal polymer material or, alternatively, could be manufactured from a metallic or non-metallic material. Drive shaft 614 includes a first axial end 620 extending distally from the shaft 614. Axial end 612 is supported for rotation within probe lower shell 582, such as by a bearing surface feature 622 molded on the inside of the probe shells 580, 582. Similarly, a second axial end 624 extends proximally from rotary drive shaft 614 and is supported in a second bearing surface feature 626, which may also be molded on the inside of probe lower shell 582. An O-ring and bushing (not shown) may be provided on each axial end 620, 624 to provide rotational support and audible noise dampening of the shaft 614 when rotary drive shaft 614 is mounted in probe lower shell 582.

As shown in FIGS. 11A, 11B, 11C, and 12, a drive carriage 634 is provided in probe assembly 532 to hold cutter gear 610, and carry the cutter gear and attached cutter 555 during translation in both the distal and proximal directions. Drive carriage 634 may be molded from a rigid polymer and has a cylindrically-shaped bore 636 extending axially therethrough. A pair of J-shaped hook extensions 640 extend from one side of drive carriage 634. Hook extensions 640 rotatably support cutter 555 on either side of cutter gear 610 to provide proximal and distal translation of the cutter gear 610 and cutter 555 during proximal and distal translation of drive carriage 634. Hook extensions 640 align cutter 555 and cutter gear 610 in the proper orientation for cutter gear teeth 612 to mesh with drive gear teeth 616.

Drive carriage 634 is supported on a translation shaft 642. Shaft 642 is supported generally parallel to cutter 555 and rotary drive shaft 614. Rotation of the translation shaft 642 provides translation of the drive carriage 634 (and so also cutter gear 610 and cutter 555) by employing a lead screw type drive. Shaft 642 includes an external lead screw thread feature, such as lead screw thread 644, on its outer surface. The screw thread 644 extends into the bore 636 in drive carriage 634. The screw thread 644 engages an internal helical threaded surface feature (not shown) provided on the inner surface of bore 636. Accordingly, as shaft 642 is rotated, the drive carriage 634 translates along the threaded feature 644 of the shaft 642. The cutter gear 610 and the cutter 555 translate with the drive carriage 634. Reversing the direction of rotation of shaft 642 reverses the direction of translation of the drive carriage 634 and the cutter 555. Translation shaft 642 may be injection molded from a rigid engineered plastic such as liquid crystal polymer material or, alternatively, could be manufactured from a metallic or non-metallic material. Translation shaft 642 with lead screw thread feature 644 may be molded, machined, or otherwise formed. Likewise, drive carriage 634 may be molded or machined to include an internal helical thread in bore 636. Rotation of shaft 642 drives the carriage and cutter gear 610 and cutter 555 in distal and proximal directions, depending upon the direction of rotation of shaft 642, so that cutter 555 translates within probe assembly 532. Cutter gear 610 is rigidly attached to cutter 555 so that the cutter translates in the same direction and at the same speed as drive carriage 634.

In one version, at the distal and proximal ends of lead screw thread 644, the helical thread is cut short so that the effective pitch width of the thread is zero. At the distal most and proximal most positions of thread 644, translation of drive carriage 634 is no longer positively driven by shaft 642 regardless of the continued rotation of shaft 642, as the carriage effectively runs off thread 644. Biasing members, such as compression coil springs 650a and 650b (FIG. 12), are positioned on shaft 642 adjacent the distal and proximal ends of screw thread 644. Springs 650a/b bias drive carriage 634 back into engagement with lead screw thread 644 when the carriage runs off thread 644. While shaft 642 continues rotating in the same direction, the zero pitch width thread in combination with springs 650a/b cause drive carriage 634 and, therefore, cutter 555 to "freewheel" at the end of the shaft. At the proximal end of the threaded portion of shaft 642, drive carriage 634 engages spring 650a. At the distal end of the threaded portion of shaft 642, drive carriage 634 engages spring 650b. When drive carriage 634 runs off screw thread 644, spring 650a or 650b engages drive carriage 634 and biases drive carriage 634 back into engagement with screw thread 644 of shaft 642, at which point continued rotation of shaft 642 again causes drive carriage 634 to run off screw thread 644. Accordingly, as long as rotation of shaft 642 is maintained in the same direction, drive carriage 634 (and cutter 555) will continue to "freewheel", with the distal end of cutter 555 translating a short distance proximally and distally as the carriage is alternately biased onto thread 644 by spring 650a or 650b and then run off screw thread 644 by rotation of shaft 642. When the cutter is in the distal most position shown in FIG. 11C, with the distal end 606 of cutter 555 positioned distal of side aperture 564, spring 650b will engage drive carriage 634, and repeatedly urge drive carriage 634 back into engagement with screw thread 644 when drive carriage 634 runs off screw thread 644. Accordingly, after cutter 555 is advanced such that the distal end 606 of cutter 555 translates distally past side aperture 564 to cut tissue, to the position shown in FIG. 11C, continued rotation of shaft 642 will result in distal end 606 oscillating back and forth, translating a short distance proximally and distally, until the direction of rotation of shaft 642 is reversed (such as to retract cutter 555 distally to the position shown in FIG. 11A). The slight movement of drive carriage 634 into engagement with screw thread 644 and out of engagement with screw thread 644 against the biasing force of spring 650b, causes the distal end 606 of cutter 555 to repetitively reciprocate a short distance within cannula 590, which distance may be about equal to the pitch of threads 644, and which distance is shorter than the distance the cutter travels in crossing side aperture 564. This reciprocal movement of cutter 555 may provide alternate covering and uncovering of at least one fluid passageway disposed distally of side aperture 564, as described below.

The zero pitch width ends of lead screw thread 644 provide a defined stop for the axial translation of cutter 555, thereby eliminating the need to slow drive carriage 634 (i.e. cutter 555) as it approaches the distal and proximal ends of the thread. This defined stop reduces the required positioning accuracy for drive carriage 634 relative to shaft 642, resulting in reduced calibration time at the initialization of a procedure. The freewheeling of drive carriage 634 at the distal and proximal most positions of translation shaft 642 eliminates the need to rotate shaft 642 a precise number of turns during a procedure. Rather, translation shaft 642 only needs to translate at least a minimum number of turns to insure drive carriage 634 has translated the entire length of lead screw thread 644 and into the zero width thread. Additionally, the freewheeling of drive carriage 634 eliminates the need to home the device, allowing probe assembly 532 to be inserted into the patient's tissue without first being attached to holster 534. After probe assembly 532 is inserted, holster 534 is attached and sampling may be commenced.

As shown in FIG. 12, a non-rotating rear tube 652 may be provided in which tube 652 may extend proximally from the proximal end of cutter 555 just proximal of cutter gear 610. Rear tube 652 may be hollow, may have substantially the same inner diameter as cutter 555, and may be comprised of the same material as cutter 555. A seal 654 may be positioned between cutter 555 and rear tube 652 to enable cutter 555 to rotate relative to rear tube 652 while providing a pneumatic seal between rear tube 652 and cutter 555. A rear lumen 656 may extend through the length of tube 652 and may be aligned with sample lumen 608 in cutter 555. Rear lumen 656 transports excised tissue samples from sample lumen 608 through probe assembly 532 to tissue storage assembly 562. Sample lumen 608 and rear lumen 656 are axially aligned to provide a continuous, generally straight lined, unobstructed passageway between side aperture 564 and tissue storage assembly 562 for the transport of tissue samples. The inner surfaces of cutter 555 and tube 652 may be coated with a hydrolubricous material to aid in the proximal transport of the excised tissue samples.

A lateral extension 658 may be provided and may be supported by and extend distally from rear tube 652 for securing the tube 652 to drive carriage 634. The extension 658 connects tube 652 to drive carriage 634 so that tube 652 translates with cutter 555, and maintains lumens 608, 656 in continuous fluid-tight communication throughout the cutting cycle.

Figure 13A:
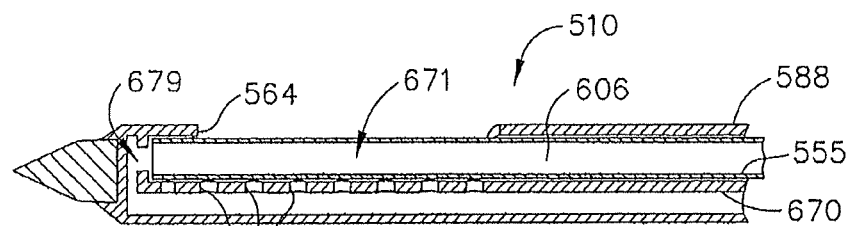
FIG. 13A is a schematic left side view in elevation of a probe of the probe assembly of FIG. 10 taken along a longitudinal center line in cross section with a cutter at a fully retracted position just proximal to a side aperture of the probe.
Figure 13B:
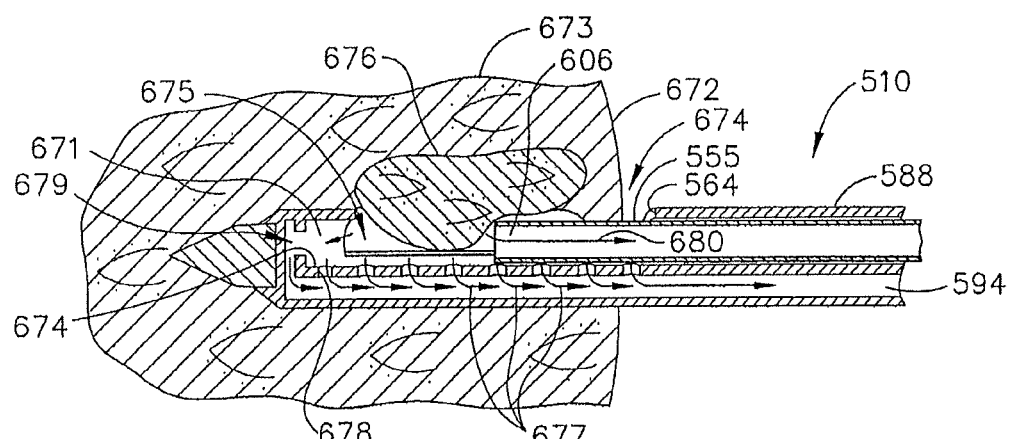
FIG. 13B is a schematic left side view in elevation of the probe of the probe assembly of FIG. 10 taken along a longitudinal center line in cross section with the cutter at a partially blocking position within a bowl of the probe below the side aperture, the exposed cutter being used to seal an insertion point into tissue as vacuum assist is used to prolapse tissue into the distal portion of the side aperture.
Figure 13C:
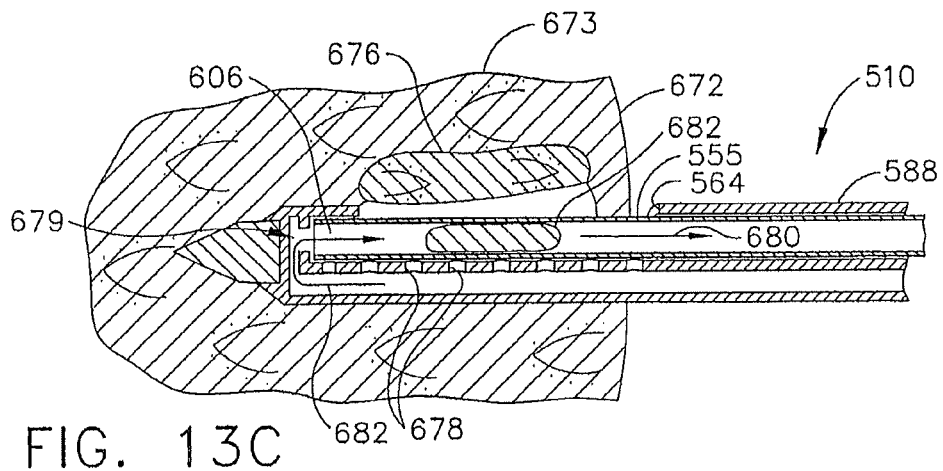
FIG. 13C is a schematic left side view in elevation of the probe of the probe assembly of FIG. 10 taken along a longitudinal center line in cross section with the cutter fully distally translated with vacuum assist being used to both push and pull a severed tissue sample in the cutter proximally.

FIGS. 13A-13C provide simplified schematic views of the movement of cutter 555 during a cutting cycle of the biopsy system 510. As shown in FIG. 13A, cutter 555 is located at a distal-most position with distal cutting end 606 disposed distally of the distal most edge of the side aperture 564. This position is similar to when the probe assembly 532 is being prepared for insertion.

With the probe assembly 532 thus positioned, the cutter 555 is retracted a preprogrammed amount, as shown in FIG. 13B. Thereby, the effective side aperture dimension is variably reduced as desired for taking a smaller length sample. The probe (needle) 588 has been inserted to point where an external surface 672 of body tissue 673 encompasses a proximal blocked portion 674 of the side aperture 564 with a distal unblocked portion 675 of the side aperture adjacent to a suspicious lesion 676. As the cutting cycle begins as depicted, a lateral vacuum force (indicated by arrow 677) may be provided in lower vacuum lumen 594. Vacuum force 677 may be transmitted from vacuum source 536 through tube 538 to lower vacuum lumen 594 through a flow path provided by union sleeve 598 (not shown in FIG. 13B). This vacuum force 677 maintains a portion of the suspicious lesion 676 in a prolapsed position inside of the bowl 671 for cutting. Microprocessor 552 may be employed to activate valve 544 to supply vacuum force 682 when switch 576 is actuated by the user to begin moving cutter 555 distally within needle 588. Lateral vacuum force 682 communicates with side aperture 564 through fluid passageways 678 disposed under side aperture 564, and through one or more fluid passageways 679 disposed distally of the side aperture 564.

Lateral vacuum force 677 may be employed in combination with an axial vacuum force 680 through sample lumen 608 to draw a tissue sample 682 into side aperture 564. After tissue sample 682 is drawn into side aperture 564, cutter 555 may be rotated and simultaneously translated distally to sever the tissue sample 682 from the surrounding tissue. While cutter 555 advances, vacuum forces 677, 680 may be maintained through lower vacuum lumen 594 and sample lumen 608 to draw the tissue sample 682 into the sample lumen 608 as the sample 682 is severed. As shown in FIG. 13B, as cutter 555 advances the cutter 555 slides across fluid passageways 678, successively blocking the lateral vacuum 677 through fluid passageways 678.

When cutter 555 reaches the distal most position, as shown in FIG. 13C, fluid passageways 678 may be completely blocked by cutter 555. With passageway 679 open, lower vacuum lumen 594 remains in fluid communication with sample lumen 608 through divider 670 despite the blocking of passageways 678.

A predefined amount of time after cutter 555 reaches its distal most position and begins to freewheel, the solenoid on rotary valve 544 may be deenergized or otherwise controlled by microprocessor 552 to replace lateral vacuum force 677 with forward pressurized air (either atmospheric or greater) as shown by the arrows 682 in FIG. 13C. The pressurized air is discharged through lateral tube 538 to vacuum lumen 594.

With port holes 678 closed off by cutter 555, the pressurized air communicates with upper cutter lumen 592 through fluid passageway 679 to apply a force against the distal face of sample 682. The "push" force acting on the distal face of sample 682 may act in combination with "pull" axial vacuum force 680 provided through sample lumen 608 of cutter 555 to move sample 682 into and through sample lumen 608 of cutter 555, as shown in FIG. 13C. Alternatively, instead of employing pressurized air to provide a force on the distal face of sample 682, a pressurized liquid, such as saline, may be directed through lower vacuum lumen 594 and fluid passageways 679 to provide the force on the distal face of sample 682. The cutter 555 closes side aperture 564 from the flow of fluid (gas or liquid) so that tissue surrounding the outer cannula and side aperture 564 is not exposed to the fluid.

As the tissue sample 682 translates proximally through probe assembly 532 towards sample collection assembly 562, cutter 555 may be maintained in a distal most position. Alternatively, cutter 555 may be retracted back through side aperture 564 towards its initial position in preparation for the next cutting cycle. After cutter 555 is retracted to its partially blocking position, and the tissue sample is translated to tissue storage assembly 562, lateral vacuum force 677 is again provided via vacuum lumen 594 to draw the next tissue sample into side aperture 564. During the translation of cutter 555, cutter 555 may operate in conjunction with divider 670 to separate cutter lumen 592 from vacuum lumen 594.

During the cutting cycle, cutter 555 translates from a point selectively either just proximal of side tissue receiving side aperture 564 or in the partially blocking position to a point just distal of side aperture 564. The severed tissue samples 682 are directed through the length of sample lumen 608 of cutter 555 and out of the proximal end of cutter 555, rather than translating with cutter 555 (with the samples carried in the distal end of the cutter) proximally through needle 588 to eject samples 682 with a knock-out pin, as in some prior devices. Accordingly, the cutting stroke length may be reduced to be just slightly longer than the length of the side aperture 564. With the reduced stroke length, the distal end of cutter 555 (as well as a length of cutter 555) may remain within needle 588 throughout the cutting cycle, eliminating the need to accommodate the full length of cutter 555 within probe housing (handle) 589 and proximal of needle 588. In addition, the reduced cutting stroke length reduces the required length of translation shaft 642, since the shaft need only translate cutter 555 a distance slightly longer than the length of side aperture 564. Reducing the translation shaft length, and eliminating the need to accommodate the cutter length within the probe housing (handle) 589, enables the length of handpiece 530 to be reduced. The time required to acquire each tissue sample is also reduced in the present invention, due to the shortened cutting stroke reducing the time required to advance and retract the cutter through cannula 590.

It should be appreciated that the biopsy system 510 advantageously supports an effectively reduced side aperture mode when desired. The reduced proximal travel of cutter 555 allows biopsy system 510 to be used on patients where the breast is compressed to a thin cross-section. Under these circumstances, biopsy needle 588 is inserted into the breast and the proximal end of side aperture 564 is not within the breast. The reduced cutter translation length effectively reduces the length of side aperture 564 preventing the sharp distal edge 606 of cutter 555 from contacting the patient's skin during each sampling cycle. The reduced cutter translation length may be preprogrammed into the microprocessor 552 located in control module 546 by the user before or during the procedure.

Shortened Distal Piercing Tip.

Figure 14:
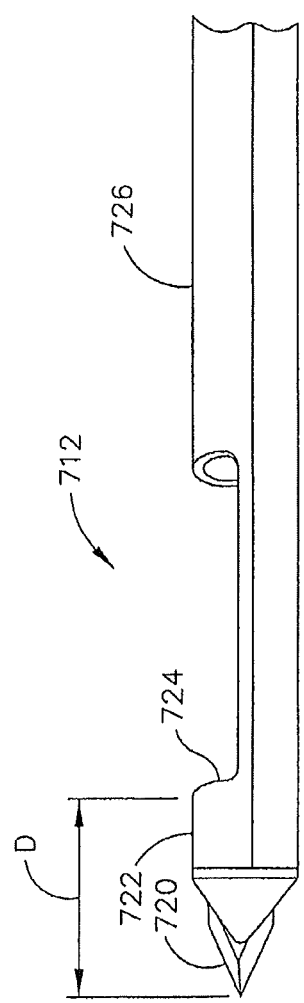
FIG. 14 is a left side view in elevation of a distal end of a probe for the probe assemblies of FIGS. 1 and 9 with a reduced length piercing tip.

In FIG. 14, a probe 712 for the probe assemblies 18, 532 advantageously includes a piercing tip 720 having a reduced longitudinal length (e.g., approximately 2 mm shorter) than generally-known piercing tips so as to reduce the "dead space" to a distal end 722 of a side aperture 724 in a cutter lumen 726. Generally known dead spaces are often about 8 mm. Thereby, lesions close to the chest wall or the medial side of the breast may be sampled without piercing as far beyond the lesion. The piercing tip 720 may be a flat blade as depicted or a pyramidal tip, a rounded cone with needle point, orthogonally crossing flat blades or other shapes.

As an alternative approach and apparatus, a piercing tip with a reduced longitudinal length may be incorporated into a obturator that extends out of a sleeve having an open distal end. Once the piercing tip reaches the surgical site, the obturator is removed and replaced with either a blunt ended stylus or a probe of a biopsy device. The blunt distal end thereof may be distally moved to occupy the location previously occupied by the piercing tip to closely approach a skin or chest wall barrier.

While preferred embodiments of the present invention have been shown and described herein, it will be obvious to those skilled in the art that such embodiments are provided by way of example only. Numerous variations, changes, and substitutions will now occur to those skilled in the art without departing from the spirit and scope of the appended claims. Additionally, each element described in relation to the invention may be alternatively described as a means for performing that element's function.

For example, a proximal blocking feature for a side aperture of a core sampling biopsy device may be integral to a probe rather than being a detachable sleeve nor a selectable position of the cutter. For instance, a guillotine door may be slidably attached to the probe, either externally or internally to the probe and either manually positioned or remotely controlled from a handle of the device as desired to shorten the side aperture.

As another example, a sleeve may include a longitudinally stepped recess such that rotation presents either a blocking position or a nonblocking position, which may be particularly applicable to circular probes. A proximally placed turn wheel on such a sleeve may provide a visual indication of the current position and the direction of rotation to change the condition.

As another example, a frangibly-attached blocking member may be formed across the proximal portion of the side aperture. When a full-sized sample is planned, this block member may be detached and disposed of.

As yet another example, a similar probe sleeve may be advantageously used with a biopsy system that does not rely upon vacuum assist (e.g., palpitating tissue into the bowl of the probe during ultrasonic imaging).

We claim:

1. A biopsy system comprising:
    (a) a probe including:
        (i) a needle configured for insertion into a tissue mass, wherein the needle includes a distal tip and a lateral aperture, wherein the lateral aperture is disposed proximally of the distal tip, wherein the lateral aperture includes a distal end and a proximal end,
        (ii) a cutter movable with respect to the needle, wherein the cutter is translatable within the needle, and
        (iii) a cutter drive assembly associated with the cutter, wherein the cutter drive assembly is configured to translate the cutter relative to the needle; and
    (b) a control unit in communication with the probe, wherein the control unit is configured to selectively drive the cutter drive assembly, wherein the control unit is configured to drive the cutter drive assembly such that the cutter is translated to a position between the distal end and the proximal end of the lateral aperture thereby providing a partially blocked lateral aperture.

2. The biopsy system of claim 1, wherein the control unit is configured to transition the cutter between a first position and a second position via the cutter drive assembly.

3. The biopsy system of claim 2, wherein the control unit is configured to selectively transition between a first operational mode and a second operational mode.

4. The biopsy system of claim 3, wherein the first operational mode corresponds to the first position of the cutter being set to a position proximal of the lateral aperture.

5. The biopsy system of claim 3, wherein the second operational mode corresponds to the first position of the cutter being set to a position between the distal end and the proximal end of the lateral aperture.

6. The biopsy system of claim 3, wherein the control unit is configured to receive a user input to selectively transition between the first operational mode and the second operational mode.

7. The biopsy system of claim 1, wherein the control unit is operable to transition to between a plurality of operational modes corresponding to operation of the biopsy probe.

8. The biopsy system of claim 1, wherein the distal tip of the needle is configured to pierce tissue.

9. The biopsy system of claim 1, wherein the needle defines a cutter lumen and a vacuum lumen, wherein the cutter is positioned within the cutter lumen.

10. The biopsy system of claim 9 further including a vacuum assistance system, wherein the vacuum lumen is in fluid communication with the vacuum assistance system.

11. The biopsy system of claim 10, wherein the vacuum assistance system is further in communication with the cutter.

12. The biopsy system of claim 1, wherein the cutter defines a cutter lumen.

13. The biopsy system of claim 12, wherein the cutter is configured to transport a severed tissue sample through the cutter lumen.

14. A biopsy device, comprising:
    (a) a piercing tube having a side aperture oriented proximally relative to a distal end of the piercing tube, wherein the side aperture defines a bowl portion within the piercing tube for receiving prolapsed tissue through the side aperture, wherein the piercing tube has an exterior and a closed distal end, wherein the piercing tube defines a longitudinal axis;
    (b) a cutter positioned within the piercing tube, wherein the cutter is longitudinally translatable within the piercing tube;
    (c) a cutter drive assembly operatively configured to distally translate the cutter across the side aperture and to sever prolapsed tissue; and
    (d) a control module, wherein the control module is in communication with the cutter drive assembly to translate the cutter between a proximal position and a distal position, wherein the proximal position of the cutter corresponds to the cutter being positioned to block at least a portion of the side aperture while also leaving at least a portion of the side aperture unblocked, wherein the control module is configured to selectively set the proximal position of the cutter such that the cutter is position to provide a plurality of different partial side aperture openings of the side aperture.

15. The biopsy device of claim 14, wherein the cutter includes a hollow tube.

16. The biopsy device of claim 14, wherein the distal position of the cutter corresponds to the cutter being position distally of the side aperture of the piercing tube.

17. The biopsy device of claim 16, wherein the cutter is configured to sever a tissue sample by transitioning from the proximal position to the distal position.

18. A biopsy system comprising:
(a) a probe including:
  (i) a needle configured for insertion into a tissue mass, wherein the needle includes a distal tip and a lateral aperture, wherein the lateral aperture is disposed proximally of the distal tip, wherein the lateral aperture includes a distal end and a proximal end,
  (ii) a cutter movable with respect to the needle, and
  (iii) a cutter drive assembly associated with the cutter, wherein the cutter drive assembly is configured to translate the cutter relative to the needle; and
(b) a control unit in communication with the probe, wherein the control unit is configured to selectively drive the cutter drive assembly, wherein the control unit is configured to drive the cutter drive assembly such that the cutter is translated to a position between the distal end and the proximal end of the lateral aperture thereby providing a partially blocked lateral aperture, wherein the control unit is configured to transition the cutter between a first position and a second position via the cutter drive assembly, wherein the control unit is configured to selectively transition between a first operational mode and a second operational mode, wherein the second operational mode corresponds to the first position of the cutter being set to a position between the distal end and the proximal end of the lateral aperture.

19. A biopsy system comprising:
(a) a probe includes:
  (i) a needle configured for insertion into a tissue mass, wherein the needle includes a distal tip and a lateral aperture, wherein the lateral aperture is disposed proximally of the distal tip, wherein the lateral aperture includes a distal end and a proximal end, wherein the needle defines a cutter lumen and a vacuum lumen,
  (ii) a cutter movable with respect to the needle, wherein the cutter is positioned within the cutter lumen of the needle, and
  (iii) a cutter drive assembly associated with the cutter, wherein the cutter drive assembly is configured to translate the cutter relative to the needle; and
(b) a control unit in communication with the probe, wherein the control unit is configured to selectively drive the cutter drive assembly, wherein the control unit is configured to drive the cutter drive assembly such that the cutter is translated to a position between the distal end and the proximal end of the lateral aperture thereby providing a partially blocked lateral aperture.

* * * * *